United States Patent
Katoh et al.

(10) Patent No.: US 10,457,628 B2
(45) Date of Patent: Oct. 29, 2019

(54) POLYMERIZABLE COMPOUND, POLYMERIZABLE COMPOSITION, FILM, AND HALF MIRROR FOR DISPLAYING PROJECTION IMAGE

(71) Applicant: FUJIFILM Corporation, Tokyo (JP)

(72) Inventors: Shunya Katoh, Ashigarakami-gun (JP); Yuki Nakazawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 235 days.

(21) Appl. No.: 15/206,449

(22) Filed: Jul. 11, 2016

(65) Prior Publication Data

US 2016/0318845 A1    Nov. 3, 2016

Related U.S. Application Data

(63) Continuation of application No. PCT/JP2015/052096, filed on Jan. 27, 2015.

(30) Foreign Application Priority Data

Jan. 28, 2014    (JP) ................................. 2014-013101

(51) Int. Cl.
   *C07C 69/90*    (2006.01)
   *C08F 20/26*    (2006.01)
   (Continued)

(52) U.S. Cl.
   CPC .............. *C07C 69/90* (2013.01); *C07C 69/75* (2013.01); *C08F 20/26* (2013.01); *C08F 22/26* (2013.01);
   (Continued)

(58) Field of Classification Search
   CPC ..... C07C 69/90; C07C 69/75; C07C 2010/14; C08F 20/26; C08F 22/26; C09K 19/3068;
   (Continued)

(56) References Cited

U.S. PATENT DOCUMENTS 3,336,362 A    8/1967    Hirzy
5,518,652 A    5/1996    Parri et al.
(Continued)

FOREIGN PATENT DOCUMENTS

JP    07-053961 A    2/1995
JP    07-109456 A    4/1995
(Continued)

OTHER PUBLICATIONS

Communication dated Apr. 18, 2017 from the State Intellectual Property Office of the P.R.C. in counterpart Application No. 201580004691.5.
(Continued)

*Primary Examiner* — Ruiyun Zhang
(74) *Attorney, Agent, or Firm* — Sughrue Mion, PLLC

(57) ABSTRACT

The present invention provides a new polymerizable compound which is represented by Formula (I). In the formula, $R^1$ indicates an alkyl group or the like, A represents a (m+n)valent cyclic group, $L_1$ indicates a single bond or the like, $L_2$ indicates —COO— or the like, Z indicates —COO— or the like, Sp indicates an alkylene group, an alkyleneoxy group, or the like, Q indicates a polymerizable group such as a (meth)acryloyl groups, l indicates an integer of 0 to 2, m indicates an integer of 1 or 2, and n indicates an integer of 1 to 3. The present invention also provides a polymerizable composition which includes the polymerizable compound described above, a film which is formed from the polymerizable composition described above, and a half mirror for displaying a projection image which includes the film described above. Using the polymerization composition described above, it is possible to manufacture films such as a low birefringence retardation film and a reflection film with high reflection wavelength region selectivity.

(Continued)

Formula (I)

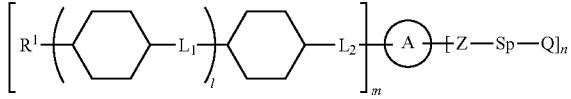

20 Claims, 1 Drawing Sheet

(51) Int. Cl.
    C09K 19/30 (2006.01)
    C09K 19/54 (2006.01)
    C07C 69/75 (2006.01)
    C08F 22/26 (2006.01)
    C09K 19/38 (2006.01)
    C09K 19/56 (2006.01)
    C09K 19/58 (2006.01)
    G02B 5/08 (2006.01)
    G02B 27/14 (2006.01)
    G03B 21/62 (2014.01)
    G02B 1/04 (2006.01)
    C09K 19/04 (2006.01)
    C09K 19/20 (2006.01)

(52) U.S. Cl.
    CPC ...... *C09K 19/3068* (2013.01); *C09K 19/3814* (2013.01); *C09K 19/54* (2013.01); *C09K 19/56* (2013.01); *C09K 19/586* (2013.01); *G02B 1/04* (2013.01); *G02B 5/0841* (2013.01); *G02B 27/142* (2013.01); *G03B 21/62* (2013.01); *C07C 2601/14* (2017.05); *C09K 2019/044* (2013.01); *C09K 2019/0448* (2013.01); *C09K 2019/2078* (2013.01); *C09K 2019/3071* (2013.01); *C09K 2019/3077* (2013.01); *Y10T 428/10* (2015.01); *Y10T 428/105* (2015.01); *Y10T 428/1036* (2015.01)

(58) Field of Classification Search
    CPC .............. C09K 19/3814; C09K 19/586; G02B 5/0841; G02B 5/30; G02B 5/3016; G03B 21/62; Y10T 428/10; Y10T 428/1036; Y10T 428/105
    USPC ....... 428/1.1, 1.3, 1.33; 252/299.01, 299.67; 349/88, 117, 183
See application file for complete search history.

(56) References Cited

U.S. PATENT DOCUMENTS

| | | | |
|---|---|---|---|
| 5,720,900 A | 2/1998 | Parri et al. | |
| 6,013,197 A | 1/2000 | Parri et al. | |
| 7,357,964 B2 | 4/2008 | Inoue et al. | |
| 8,007,682 B2 | 8/2011 | Shioya et al. | |
| 8,771,810 B2 | 7/2014 | Mizumura et al. | |
| 2005/0012070 A1 | 1/2005 | Inoue et al. | |
| 2009/0128769 A1* | 5/2009 | Shioya | C09K 19/3068 349/183 |
| 2012/0224245 A1* | 9/2012 | Adlem | C09K 19/3059 359/245 |
| 2013/0109825 A1 | 5/2013 | Mizumura et al. | |
| 2015/0079380 A1* | 3/2015 | Muramatsu | C09K 19/3447 428/220 |

FOREIGN PATENT DOCUMENTS

| | | | |
|---|---|---|---|
| JP | 10-195138 A | | 7/1998 |
| JP | 2004-189715 A | | 7/2004 |
| JP | 2004-262884 A | | 9/2004 |
| JP | 2006-265527 A | | 10/2006 |
| JP | 2006265527 A | * | 10/2006 |
| JP | 2009-120547 A | | 6/2009 |
| JP | 2010-031223 A | | 2/2010 |
| JP | 2013-216591 A | | 10/2013 |
| WO | 2008/091090 A1 | | 7/2008 |
| WO | 2008/143470 A2 | | 11/2008 |
| WO | 2011/036080 A1 | | 3/2011 |
| WO | 2011/162291 A1 | | 12/2011 |

OTHER PUBLICATIONS

Office Action dated Jul. 4, 2017, issued by the Korean Intellectual Property Office in corresponding Korean Application No. 10-2016-7020450.
International Preliminary Report on Patentability of PCT/JP2015/052096 dated Jan. 5, 2016.
Written Opinion of PCT/JP2015/052096 dated Mar. 31, 2015.
International Search Report of PCT/JP2015/052096 dated Mar. 31, 2015.
Zhurnal Prikladnoi Khimii, 1983, 56(10), pp. 2312-2317.
Arnaud, et al., "Potent and Fully Noncompetitive Peptidomimetic Inhibitor of Multidrug Resistance P-Glycoprotein", Journal of Medicinal Chemistry, 2010, vol. 53, No. 18, pp. 6720-6729, and Supporting Information on pp. S1-S23 (33 pages).
Office Action dated Nov. 22, 2016 from the Japanese Patent Office in counterpart Japanese Application No. 2014-181136.
International Preliminary on Patentability Report dated Jul. 28, 2016, issued by the International Searching Authority in Application No. PCT/JP2015/052096.

* cited by examiner

POLYMERIZABLE COMPOUND, POLYMERIZABLE COMPOSITION, FILM, AND HALF MIRROR FOR DISPLAYING PROJECTION IMAGE

CROSS-REFERENCE TO RELATED APPLICATIONS

This application is a continuation of PCT International Application No. PCT/JP2015/052096 filed on Jan. 27, 2015, which claims priority under 35 U.S.C § 119 (a) to Japanese Patent Application No. 2014-013101 filed on Jan. 28, 2014, the entire content of which is incorporated herein by reference.

BACKGROUND OF THE INVENTION

1. Field of the Invention

The present invention relates to a new polymerizable compound. The present invention also relates to a polymerizable composition which includes the polymerizable compound described above and a film which is formed from the polymerizable composition described above.

2. Description of the Related Art

It is possible to produce various optical films such as a retardation film and a reflection film using a polymerizable compound which has a liquid-crystalline property. The birefringence of the polymerizable compound is one of the properties which greatly influences the optical properties of the obtained optical film. For example, it is possible to obtain a retardation film which has a desired phase difference with a thin film thickness by using a liquid crystal which exhibits high birefringence (WO2011/162291A).

On the other hand, it is possible to obtain a reflection film with high reflection wavelength region selectivity by fixing a cholesteric liquid crystalline phase, which is formed using a polymerizable compound with low birefringence, to a film. JP2004-262884A discloses that a low birefringence retardation film or a reflection film with high reflection wavelength region selectivity are obtained by using non-liquid-crystalline (meth)acrylate compound with a specific structure along with a polymerizable liquid crystal compound.

SUMMARY OF THE INVENTION

The present invention has an object of providing a new polymerizable compound which is able to be used as a low birefringence liquid crystal. The present invention also has an object of providing films such as a low birefringence retardation film, and a reflection film with high reflection wavelength region selectivity.

While researching compounds with various structures to solve the problems described above, the present inventors discovered that a new compound with a similar structure to that of the polymerizable compounds which are well known from WO2008/143470A or WO2008/091090A exhibits low birefringence and also has properties which are advantageous for forming a film, carried out further research based on this discovery, and completed the present invention.

That is, the present invention provides <1> to <23> below.

<1> A polymerizable compound which is represented by Formula (I):

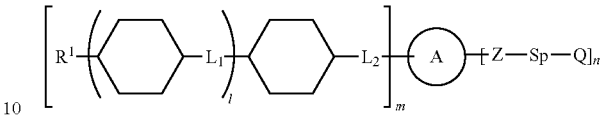

in the formula, $R^1$ indicates a hydrogen atom, a straight-chain or branched alkyl group with 1 to 12 carbon atoms, or —Z-Sp-Q,

The moiety indicated above represents a (m+n)valent cyclic group, $L_1$ indicates a single bond, —COO—, or —OCO—,
$L_2$ indicates —COO—, —OCO—, or —CONR$^2$—,
Z indicates a single bond, —O—, —NH—, —N(CH$_3$)—, —S—, —COO—, —OCO—, —OCOO—, or —CONR$^2$—,
$R^2$ indicates a hydrogen atom or -Sp-Q,
Sp indicates a single bond, a straight-chain or branched alkylene group with 1 to 12 carbon atoms which may be substituted with Q, or a linking group which is obtained by substituting any one or more of —CH$_2$— with —O—, —S—, —NH—, —N(Q)-, or —CO— in a straight-chain or branched alkylene group with 1 to 12 carbon atoms which may be substituted with Q,
Q indicates a hydrogen atom or a polymerizable group,
l indicates an integer of 0 to 2,
m indicates an integer of 1 or 2,
n indicates an integer of 1 to 3,
a plurality of $R^1$'s, a plurality of $L_1$'s, a plurality of $L_2$'s, a plurality of l's, a plurality of Z's, a plurality of Sp's, and a plurality of Q's may be each the same as or different from each other, and
as —Z-Sp-Q, at least one group where Z is —COO— or —CONR$^2$— and Q is a polymerizable group is included.

<2> The polymerizable compound according to <1>, in which all of $L_1$'s are single bonds and all of $L_2$'s are —COO— or —CONR$^2$—.

<3> The polymerizable compound according to <1> or <2>, in which all of Q's are any one of polymerizable groups below.

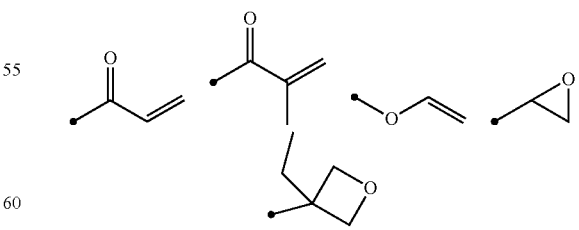

<4> The polymerizable compound according to any one of <1> to <3>, in which all of l's are 1.

<5> The polymerizable compound according to any one of <1> to <4>, in which all of $R^1$'s are straight-chain alkyl groups.

<6>

The polymerizable compound according to any one of <1> to <5>, in which the moiety indicated above is a group which is obtained by removing (m+n) hydrogen atoms from benzene.

<7> The polymerizable compound according to <1>, in which all of $R^1$'s are straight-chain alkyl groups, all of l's are 1, all of $L_1$'s are single bonds, all of $L_2$'s are —COO—.

The moiety indicated above is a group which is obtained by removing (m+n) hydrogen atoms from benzene, and all of Q's are (meth)acryloyl groups.

<8> The polymerizable compound according to <7>, in which m is 1, n is 1 or 2, and at least one of Z is —COO—.

<9> The polymerizable compound according to <7>, in which m is 2, n is 1, and Z is —COO— or —CONR²—.

<10> A polymerizable composition comprising the polymerizable compound according to any one of <1> to <9>.

<11> The polymerizable composition according to <10>, further comprising another polymerizable liquid crystal compound other than the polymerizable compound which is represented by Formula (I).

<12> The polymerizable composition according to <10> or <11>, further comprising a cross-linking agent.

<13> The polymerizable composition according to any one of <10> to <12>, further comprising two or more types of polymerizable compounds which are represented by Formula (I).

<14> The polymerizable composition according to any one of <10> to <13>, further comprising a polymerization initiator.

<15> The polymerizable composition according to any one of <10> to <14>, further comprising a chiral compound.

<16> A film comprising a layer which is formed from the polymerizable composition according to any one of <10> to <15>.

<17> A film comprising two or more layers which are formed from the polymerizable composition according to any one of <10> to <15>.

<18> The film according to <16> or <17>, in which selective reflection is exhibited, and Δλ/λ which is a ratio of a half-value width Δλ of a wavelength region of the selective reflection to a center wavelength λ of the selective reflection is 0.09 or less.

<19> The film according to any one of <16> to <18>, in which visible light is reflected.

<20> A film comprising at least three layers which are formed from the polymerizable composition according to any one of <10> to <15>, in which the three layers are a layer in which a cholesteric liquid crystalline phase which has a center wavelength of selective reflection in a red light wavelength region is fixed, a layer in which a cholesteric liquid crystalline phase which has a center wavelength of selective reflection in a green light wavelength region is fixed, and a layer in which a cholesteric liquid crystalline phase which has a center wavelength of selective reflection in a blue light wavelength region is fixed.

<21> A half mirror for displaying a projection image comprising the film according to <20>.

<22> The half mirror for displaying a projection image according to <20>, further comprising a substrate which is inorganic glass or an acrylic resin.

<23> The half mirror for displaying a projection image according to <21> or <22>, further comprising an anti-reflection layer on an uppermost surface.

According to the present invention, a new polymerizable compound which is able to be used as a low birefringence liquid crystal is provided. According to the present invention, new films such as a low birefringence retardation film or a reflection film with high reflection wavelength region selectivity are also provided.

DESCRIPTION OF THE PREFERRED EMBODIMENTS

Figure 1:
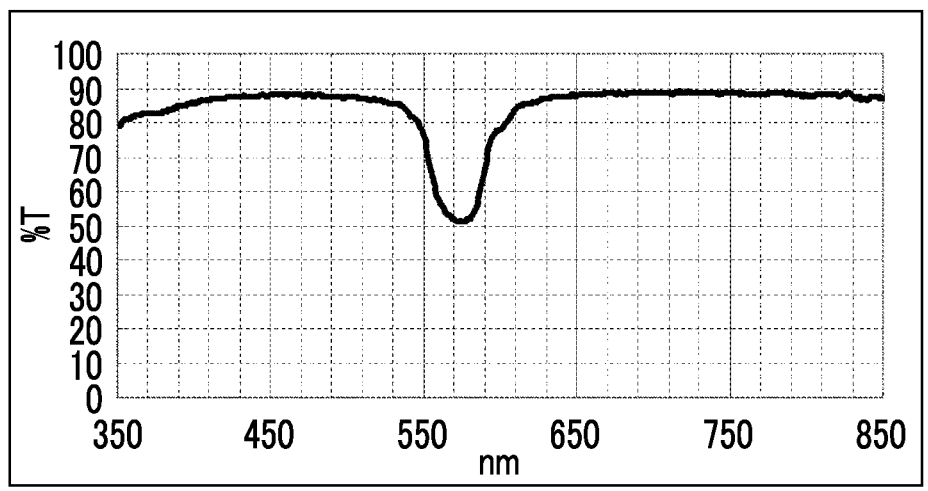
FIG. 1 is a diagram which shows the transmission spectrum of a reflection film which is produced in Examples.

Detailed description will be given below of the present invention. Here, the numeric value ranges which are represented by "to" in the present specification signify ranges which include the numeric values described before and after the "to" as the lower limit value and the upper limit value.

In the present specification, description of "(meth)acrylate" represents the meaning of "one of or both of acrylate and methacrylate". The same applies to a "(meth)acryl group" and the like, and a "(meth)acryloyl group" represents the meaning of "one of or both of an acryloyl group and a methacryloyl group".

<Polymerizable Compound Represented by Formula (I)>

Description will be given below of each group in Formula (I).

The cyclohexyl groups in Formula (I) are all trans-1,4-cyclohexyl groups.

In Formula (I), $R^1$ indicates a hydrogen atom, a straight-chain or branched alkyl group with 1 to 12 carbon atoms, or —Z-Sp-Q. $R^1$ is preferably a straight-chain or branched alkyl group with 1 to 12 carbon atoms or —Z-Sp-Q, and more preferably a straight-chain or branched alkyl group with 1 to 12 carbon atoms. The straight-chain or branched alkyl group preferably has 1 to 5 carbon atoms, and more preferably has 2 to 4 carbon atoms. $R^1$ is preferably a straight-chain alkyl group, and particularly preferably an ethyl group or an n-butyl group.

Description will be given below of —Z-Sp-Q.

In Formula (I), the moiety indicated below represents a (m+n)valent cyclic group.

That is, the moiety represents a portion other than m+n substituent groups in a structure formed by bonding m+n substituent groups in a cyclic compound.

The cyclic compound may be an aromatic cyclic compound or may be an aliphatic cyclic compound. In addition, the cyclic compound may be a monocyclic compound or may be a fused ring compound which includes two or more rings. In addition, regarding the cyclic compound, the ring may be only formed by carbon atoms or the ring may be formed to include atoms other than carbon atoms. For example, one or two or more atoms selected from a nitrogen atom, a sulfur atom, or an oxygen atom may be included. The number of atoms which form the ring is not particularly limited; however, approximately 5 to 18 is sufficient, 5 to 10 is preferable, 5 to 7 is more preferable, and 6 is particularly preferable. Examples of the cyclic compound include an aliphatic hydrocarbon ring compound of a 5-membered to 18-membered ring, an aromatic hydrocarbon ring compound of a 5-membered to 18-membered ring, or an aromatic hetero ring compound of a 5-membered to 18-membered ring. Among these, the aromatic hydrocarbon ring compound of a 5-membered to 18-membered ring is particularly preferable.

Examples of cyclic compounds will be shown below; however, the present invention is not limited thereto.

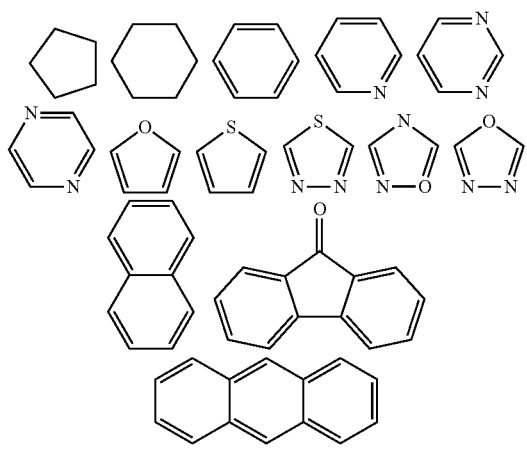

Specifically, the cyclic compound is preferably benzene or cyclohexane, and particularly preferably benzene.

The bonding position of (m+n) substituent groups to the cyclic compound is not particularly limited; however, at least two substituent groups are preferably not bonded to adjacent atoms. In a case where the cyclic compound is benzene, at least two substituent groups are preferably at a meta-position or para-position, and particularly preferably at a para-position.

In Formula (I), $L_1$ indicates a single bond, —COO—, or —OCO—. $L_1$ is preferably a single bond.

In Formula (I), $L_2$ indicates —COO—, —OCO—, or —CONR$^2$—. R$^2$ indicates a hydrogen atom or -Sp-Q. Description will be given below of Sp and Q. R$^2$ is preferably a hydrogen atom. $L_2$ is preferably —COO— or —CONR$^2$—.

In Formula (I), Z indicates a single bond, —O—, —NH—, —N(CH$_3$)—, —S—, —COO—, —OCO—, —OCOO—, or —CONR$^2$—. Z is preferably —COO—, —OCO—, —OCOO—, or —CONR$^2$—, more preferably —COO— or —CONR$^2$—, and particularly preferably —COO—.

In Formula (I), Sp indicates a single bond, a straight-chain or branched alkylene group with 1 to 12 carbon atoms which may be substituted with Q, or a linking group which is obtained by substituting any one or more of —CH$_2$— with —O—, —S—, —NH—, —N(Q)-, or —CO— in a straight-chain or branched alkylene group with 1 to 12 carbon atoms which may be substituted with Q. Where "may be substituted with Q" is used, it is sufficient to have one, two, three, four, or five or more of Q as substituent groups. The substitution position of Q is not particularly limited; however, examples of preferable positions include the terminal of a branched group and the like. In a straight-chain or branched alkylene group with 1 to 12 carbon atoms which may be substituted with Q, when any one or more of —CH$_2$— are substituted with other groups, the position thereof may be any position. Preferable examples include an alkylene group in which —CH$_2$— of a terminal which is bonded to Q is substituted with —O— or —NH—. In addition, other preferable examples include an alkylene group in which a plurality of —CH$_2$— other than the terminal —CH$_2$— are substituted every 2 to 4 —CH$_2$—. As other groups which may be substituted, —O— or —NH— are preferable, and —O— is more preferable. Among the above, Sp is preferably an unsubstituted straight-chain alkylene group with 1 to 12 carbon atoms, a group which is linked to an unsubstituted straight-chain alkylene group with 1 to 11 carbon atoms on the terminal side in which —O— or —NH— are bonded to Q, a branched alkylene group with 1 to 12 carbon atoms which has Q which is not a hydrogen atom (that is, Q which is a polymerizable group) at all the terminals, a group which is linked to a branched alkylene group with 1 to 11 carbon atoms which has Q which is not a hydrogen atom (that is, Q which is a polymerizable group) at all the terminals at the terminal side on which —O— or —NH— are bonded to Q, a diethylene oxide group, a group which is linked to a diethylene oxide group at the terminal side in which —O— or —NH— are bonded to Q, a triethylene oxide group, a group which is linked to a triethylene oxide group at the terminal side in which —O— or —NH— are bonded to Q, and the like. A group which is represented by Sp preferably has 1 to 8 carbon atoms, more preferably 1 to 6 carbon atoms, and even more preferably 2 to 4 carbon atoms.

In Formula (I), Q indicates a hydrogen atom or a polymerizable group. The polymerizable group which is represented by Q is not particularly limited; however, a polymerizable group for which radical polymerization or cation polymerization is possible is preferable. It is possible to use radical polymerizable groups which are generally known as the radical polymerizable group and examples of suitable radical polymerizable groups include a (meth)acryloyl group. In this case, regarding the polymerization speed, it is known that an acryloyl group is generally fast and an acryloyl group is preferable from the point of view of improving the productivity; however, it is also possible to use a methacryloyl group as the polymerizable group of a high birefringence liquid crystal in the same manner. It is possible to use cation polymerizable groups which are generally known as cation polymerizable groups and examples thereof specifically include an alicyclic ether group, a cyclic acetal group, a cyclic lactone group, a cyclic thioether group, a spiro ortho ester group, a vinyloxy group, and the like. Among these, an alicyclic ether group and a vinyloxy group are suitable, and an epoxy group, an oxetanyl group, and a vinyloxy group are particularly preferable.

Particularly preferable examples of Q include the following.

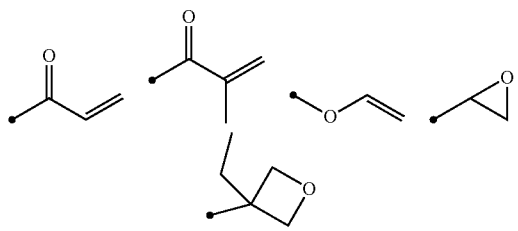

The polymerizable group which is represented by Q is preferably a (meth)acryloyl group, and more preferably an acryloyl group.

Formula (I) may have a (meth)acryloyloxy group which is formed by some of Q's and Sp's and preferably has an acryloyloxy group.

In Formula (I), l indicates an integer of 0 to 2 and is preferably 1. m indicates an integer of 1 or 2. n indicates an integer of 1 to 3 and is preferably 1 or 2. m+n is preferably 2 or 3.

In Formula (I), there are cases where a plurality of $R^1$'s, $L_1$'s, $L_2$'s, l's, Z's, Sp's, and Q's are each present according to the integers which are defined by l, m, and n. The plurality of $R^1$'s, the plurality of $L_1$'s, the plurality of $L_2$'s, the plurality of l's, the plurality of Z's, the plurality of Sp's, and the plurality of Q's in this case may be the same as or different from each other.

In addition, Formula (I) includes at least one of —Z-Sp-Q in which Z is —COO— or —CONR²— and Q is a polymerizable group (Q is not a hydrogen atom) as —Z-Sp-Q. That is, a compound which is represented by Formula (I) has at least one polymerizable group and also includes a —CO— group which is directly bonded to the moiety indicated below.

(A)

The polymerizable compound which is indicated by Formula (I) is preferably a compound in which all of $R^1$'s are straight-chain alkyl groups, all of l's are 1, all of $L_1$'s are single bonds, all of $L_2$'s are —COO—, the cyclic compound is benzene, and all of Q's are (meth)acryloyl groups. Furthermore, at this time, a compound in which m is 1, n is 1 or 2, and at least one Z is —COO—, or a compound in which m is 2, n is 1, and Z is —COO— or —CONR²— is particularly preferable.

Examples of the polymerizable compound which is indicated by Formula (I) will be shown below; however, the present invention is not limited thereto.

1

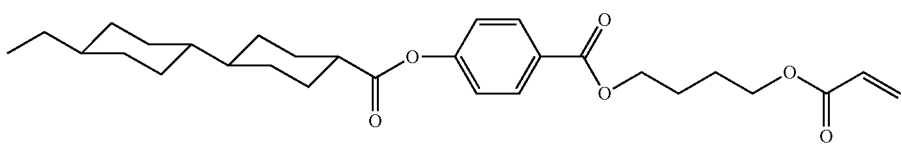

2

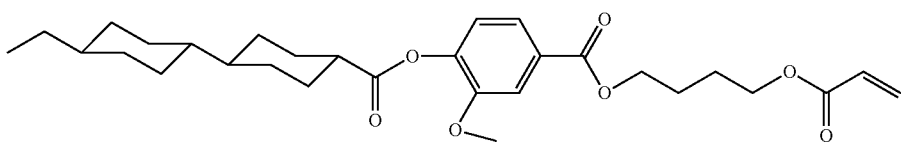

3

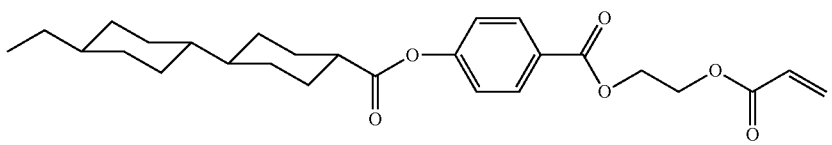

4

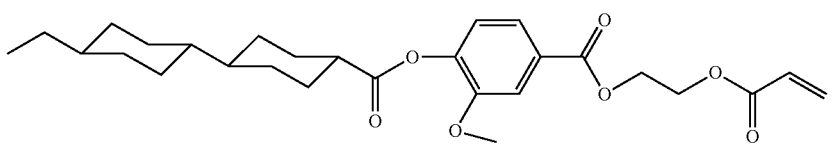

5

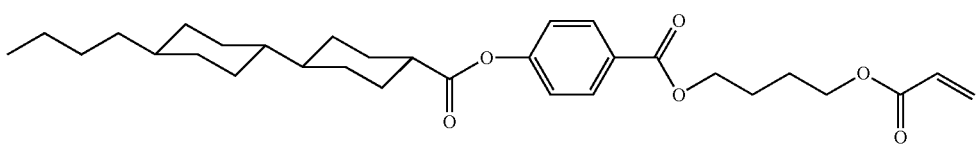

6

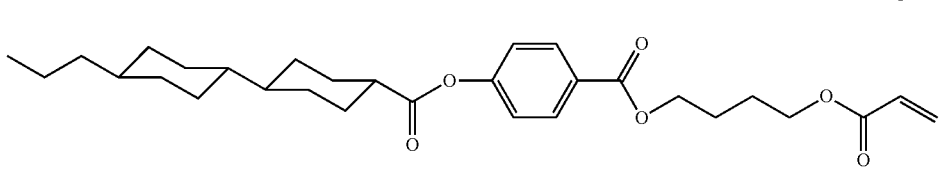

7
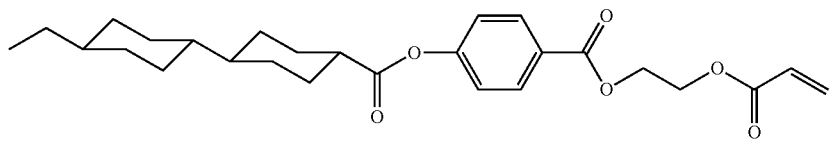
8
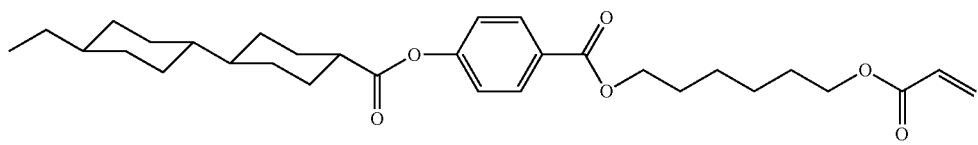
9
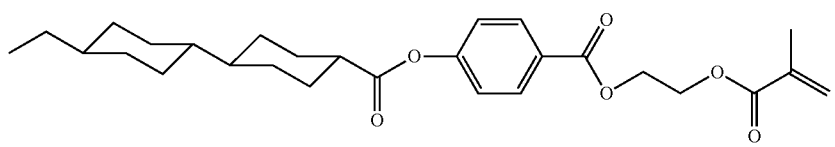
10
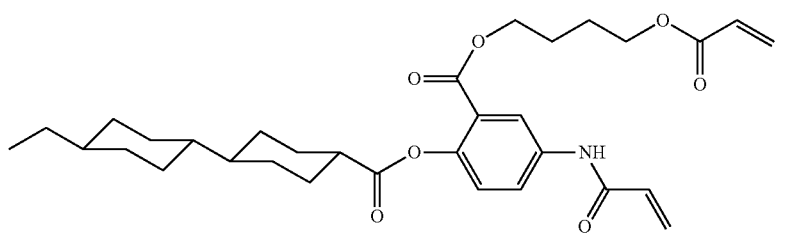
11
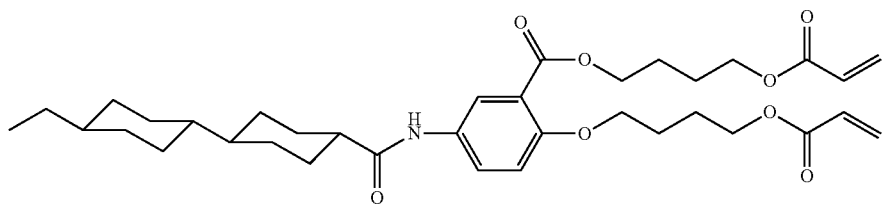
12
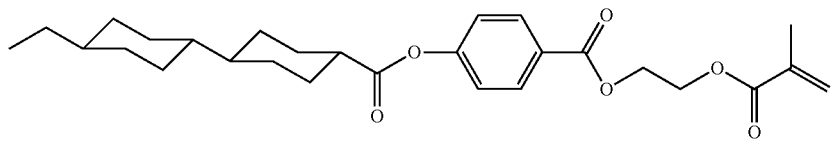
13
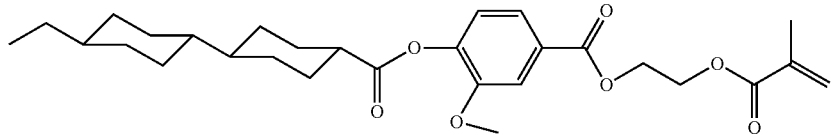
14
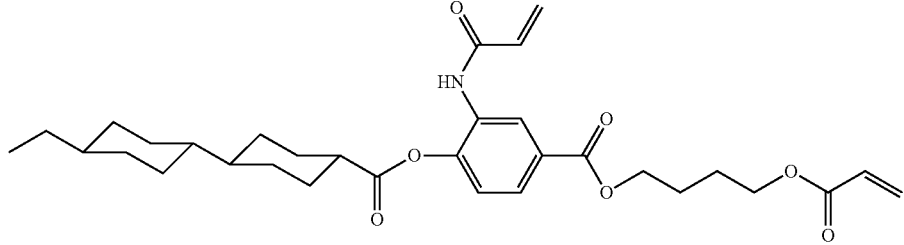
15
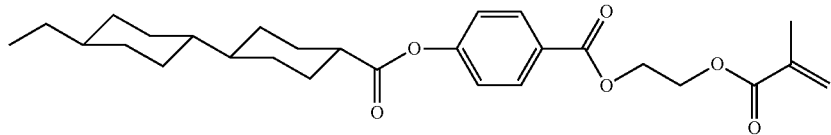

-continued
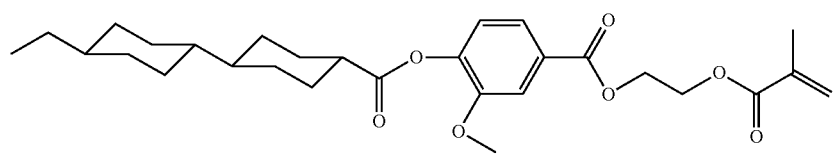
16
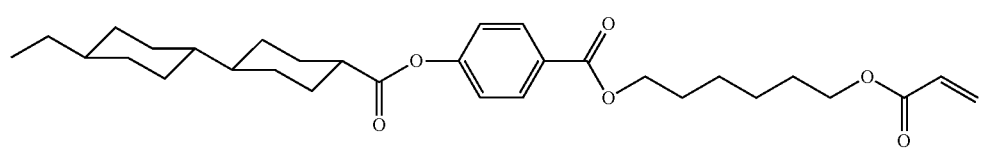
17
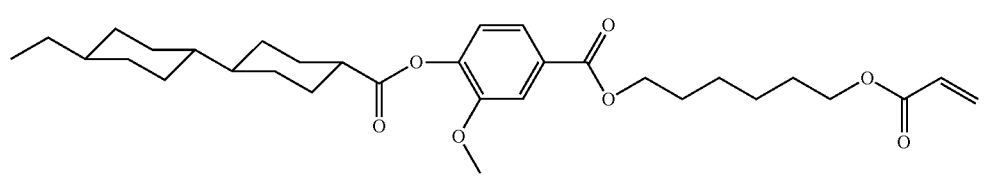
18
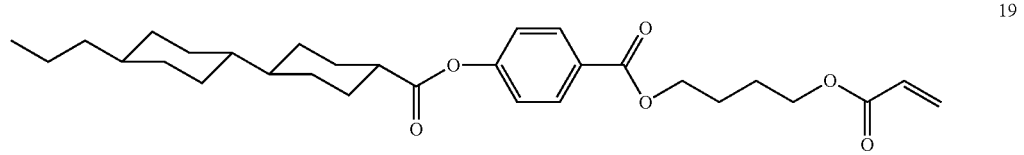
19
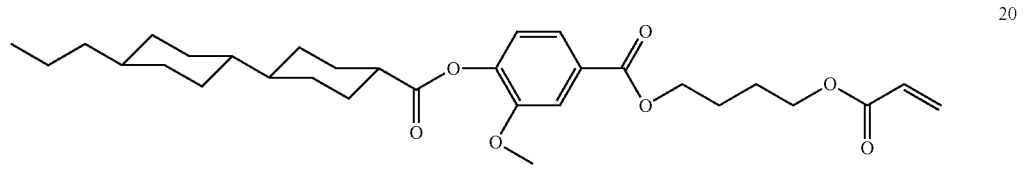
20
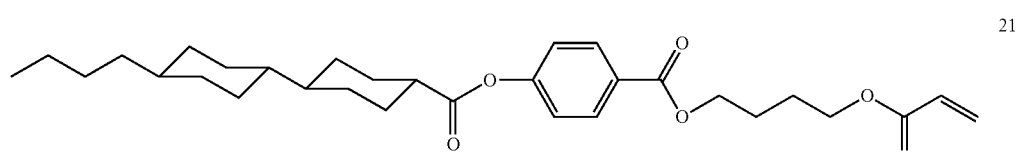
21
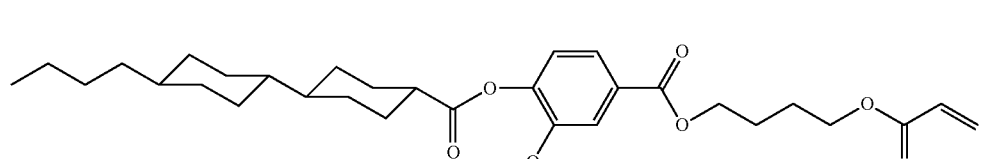
22
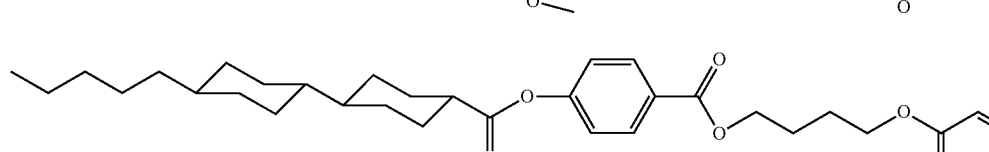
23
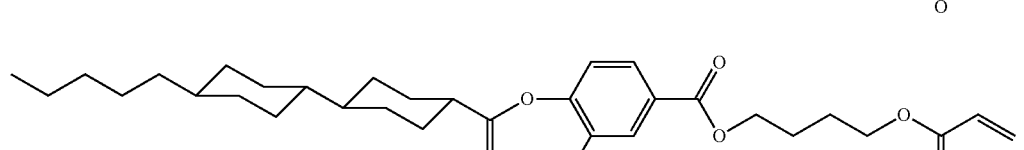
24
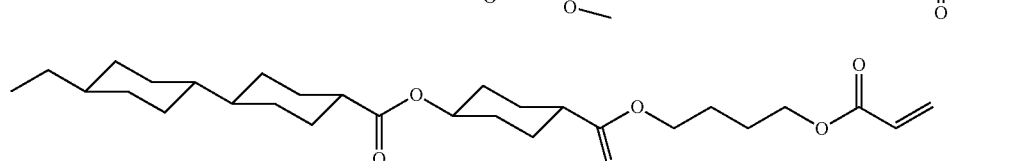
25

26
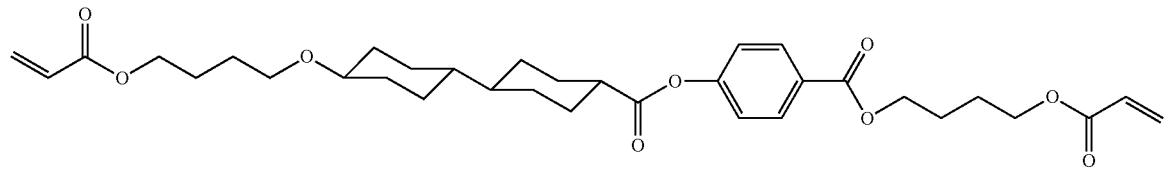
27
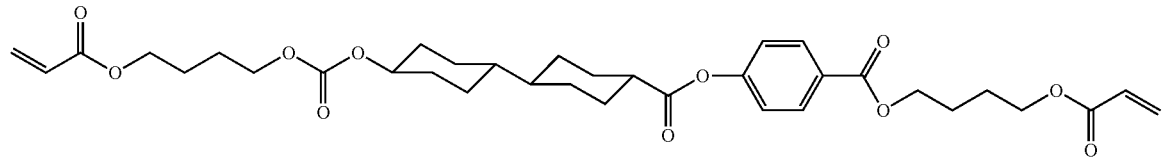
28
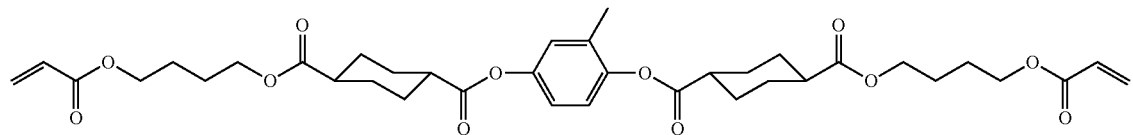
29
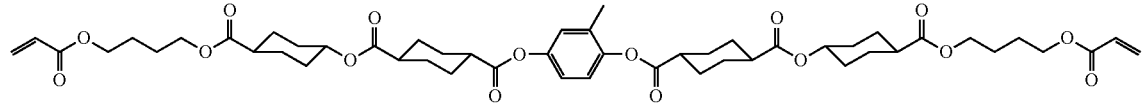
30
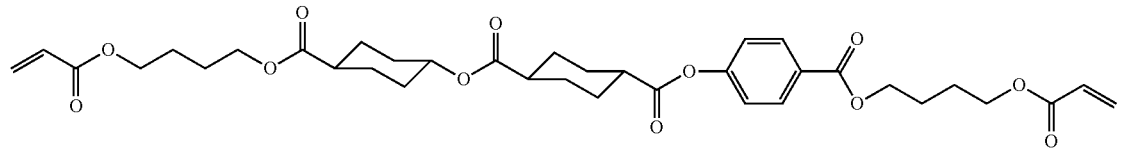
31
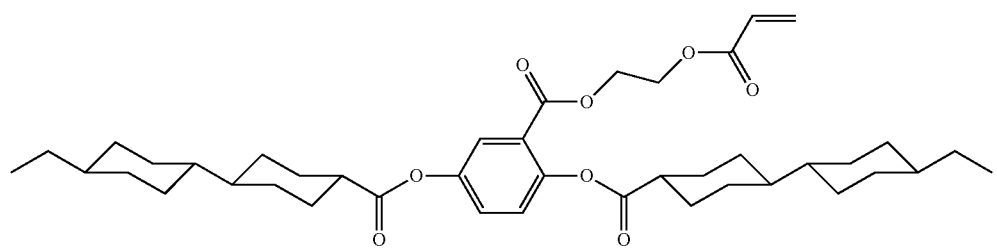
32
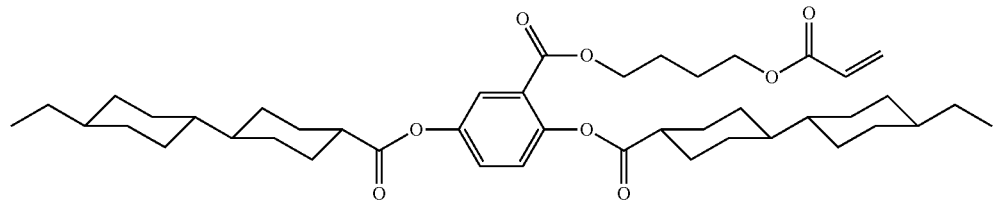
33
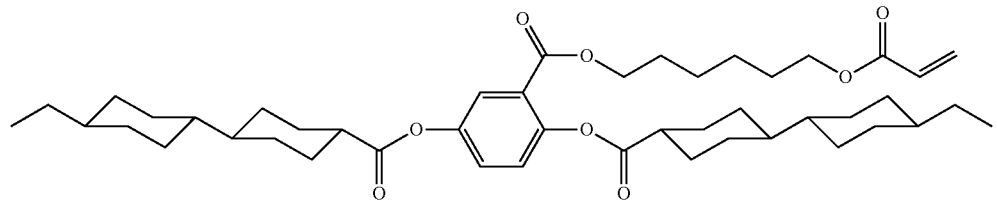

-continued
34
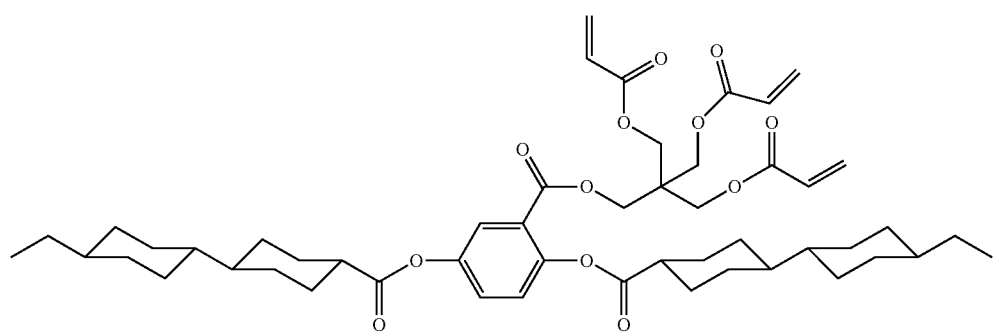
35
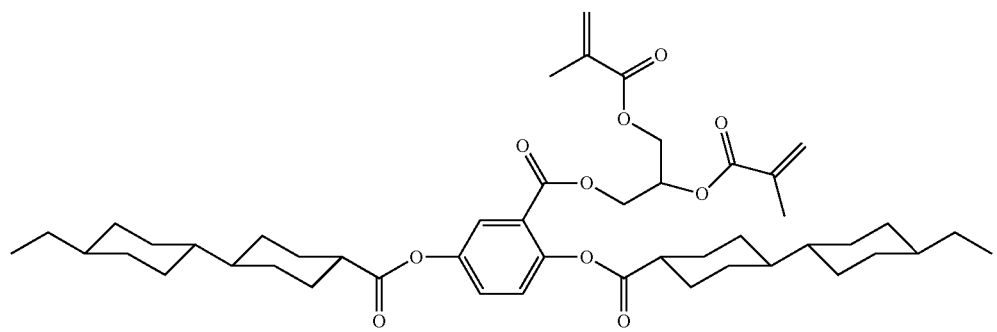
36
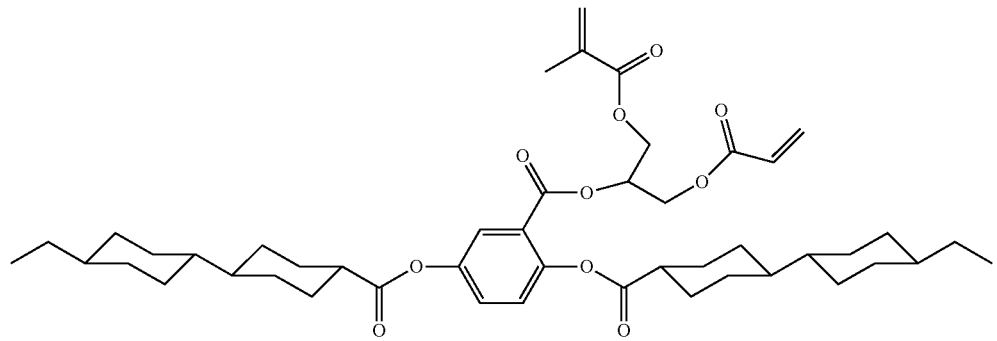
37
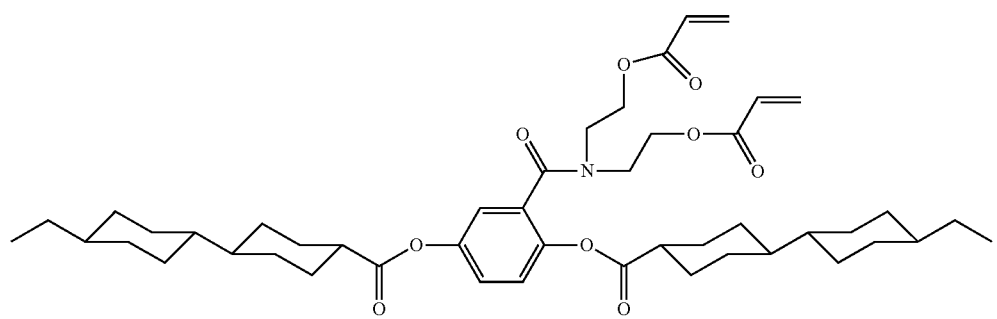
38
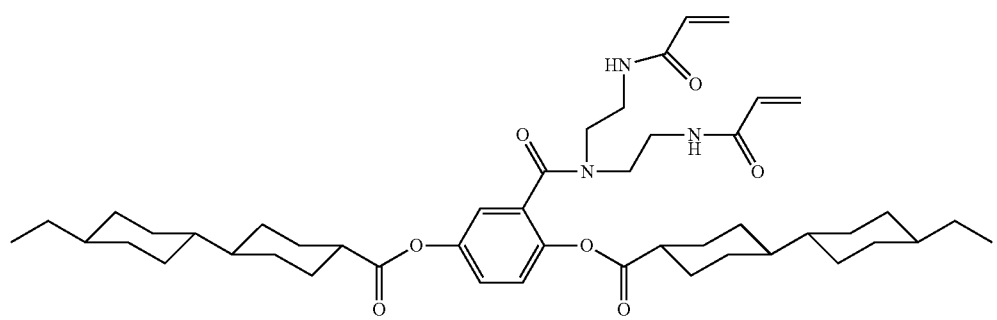

39
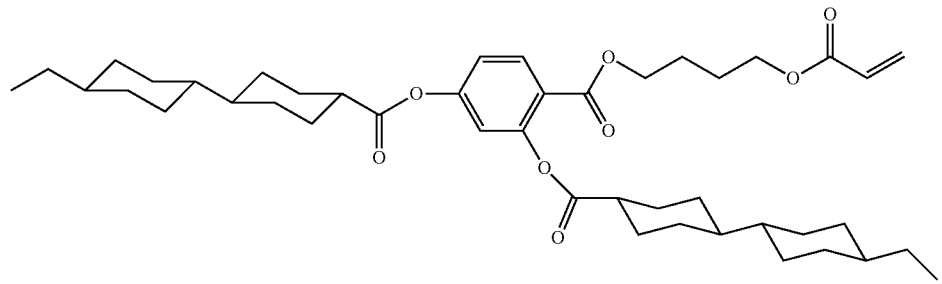
40
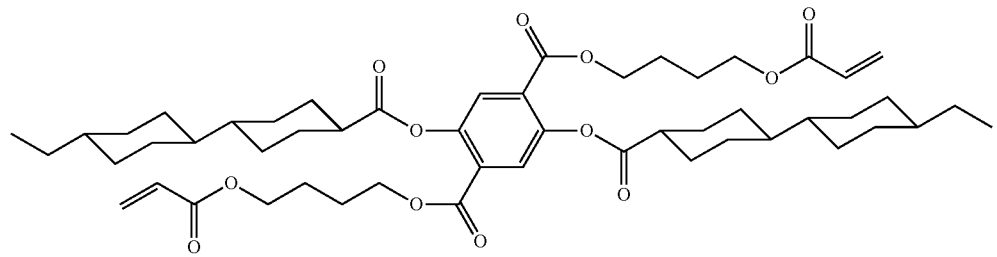
41
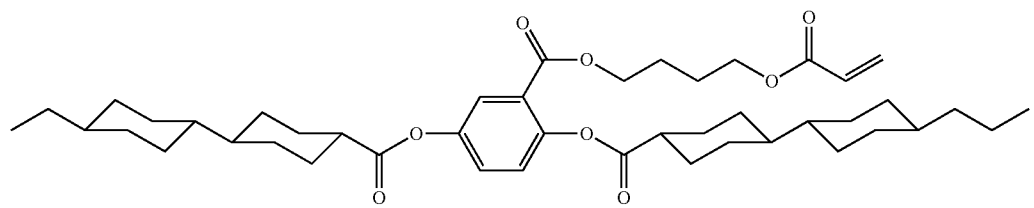
42
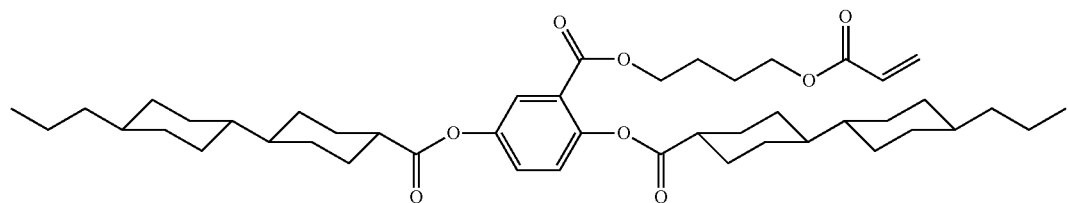
43
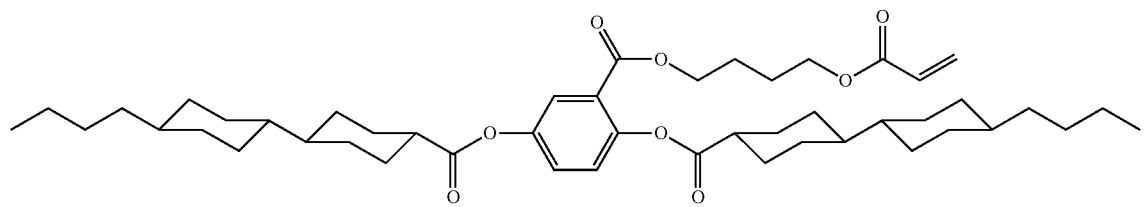
44
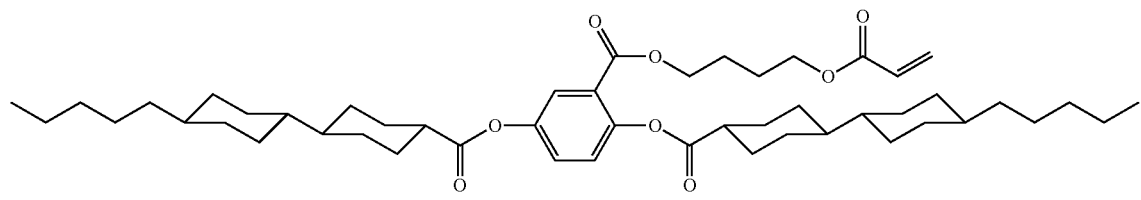
45
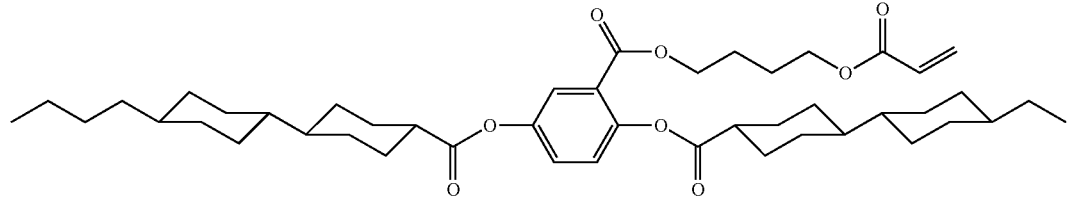

-continued
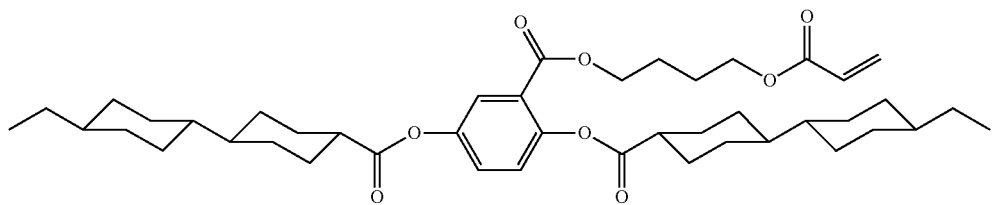
46
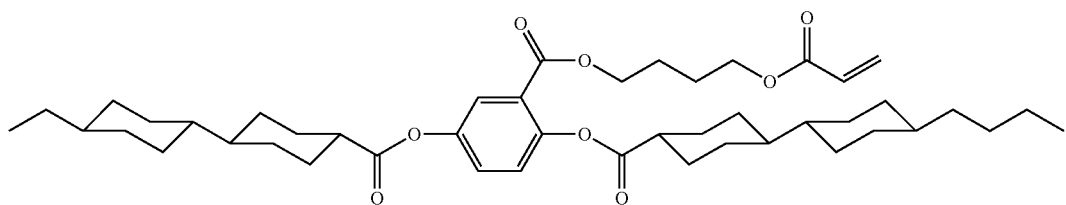
47
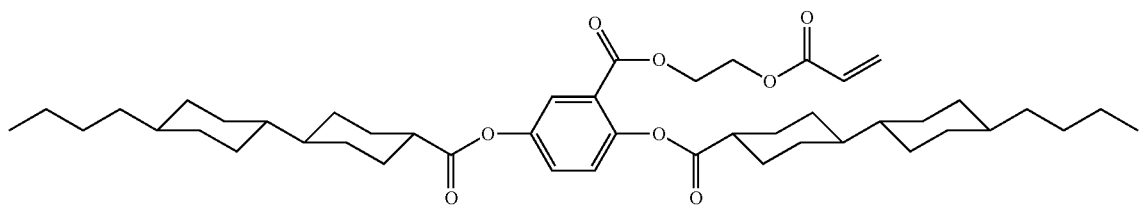
48
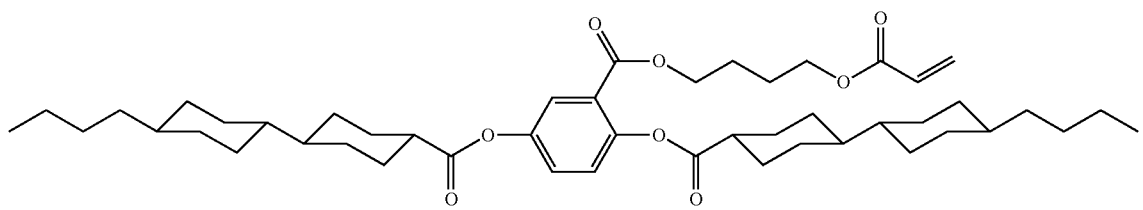
49
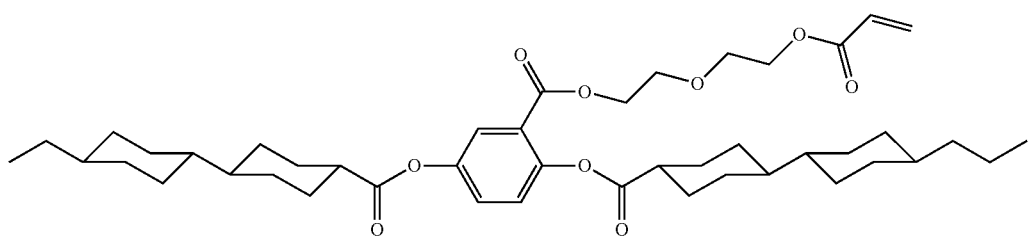
50
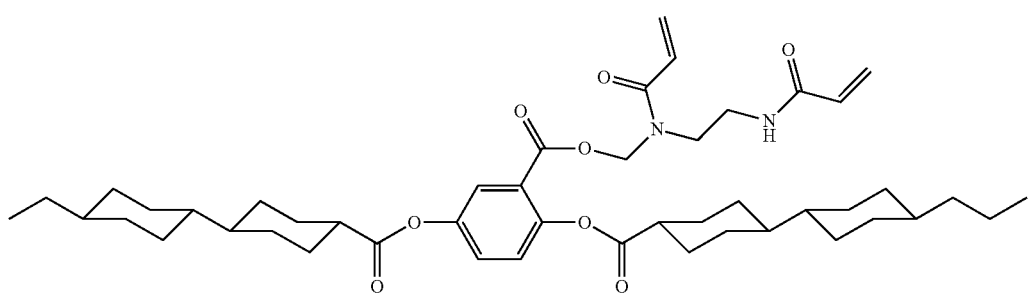
51

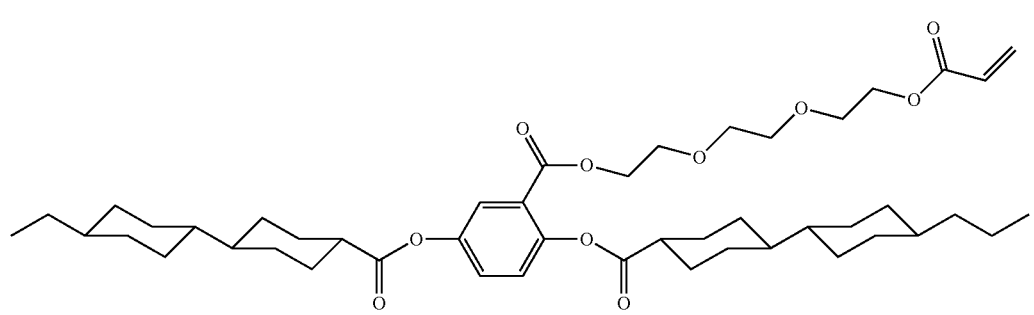
52
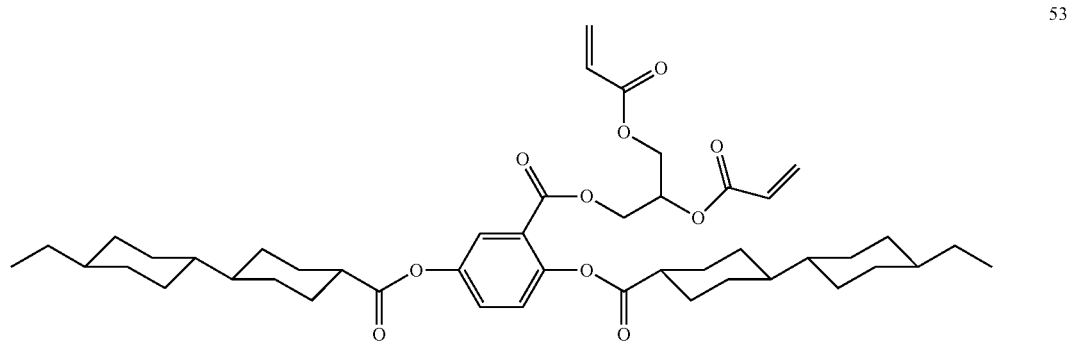
53
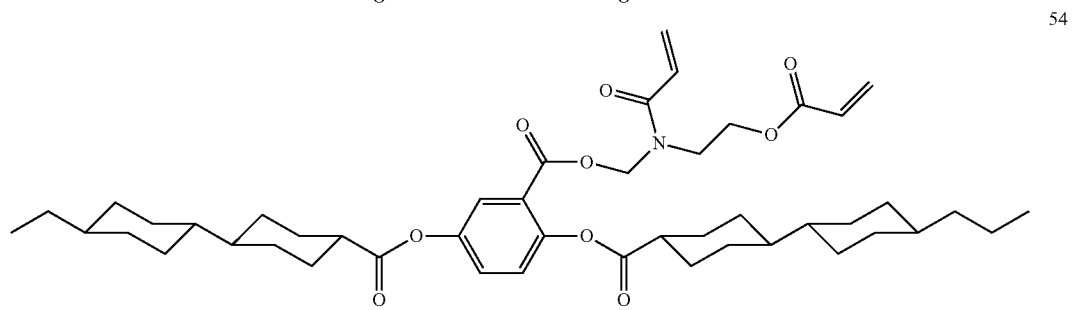
54
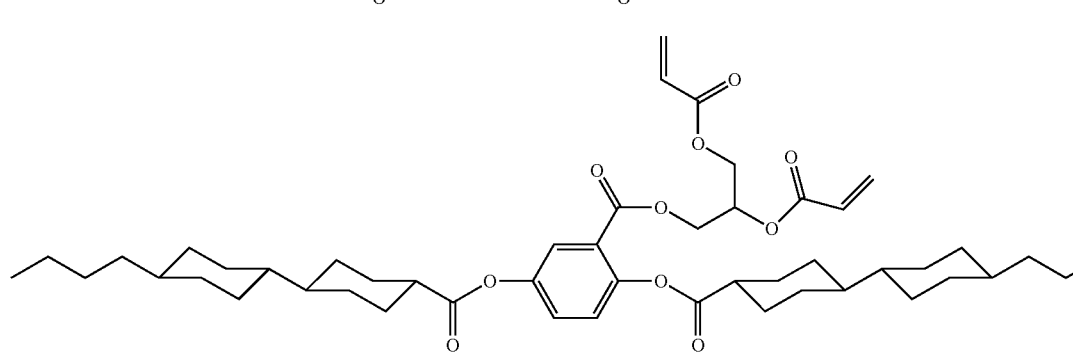
55
It is possible to produce the polymerizable compound which is indicated by Formula (I) by a well-known method and, for example, it is possible to produce the polymerizable compound by the method below.
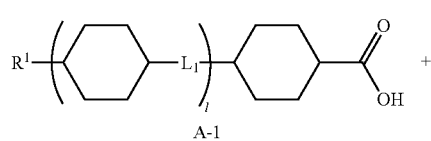
A-1
-continued
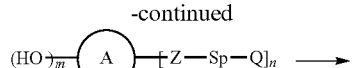
A-2
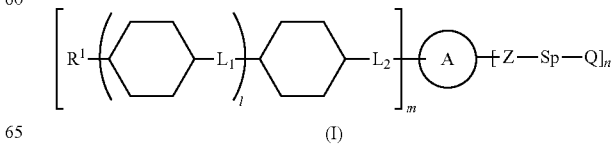
(I)

For example, in a case where $L_2$ is —COO—, it is possible to produce the polymerizable compound by esterifying a carboxylic acid derivative A-1 using a phenol (or alcohol) derivative A-2.

Examples of an esterification reaction method include a method of making the carboxylic acid derivative A-1 into an acid chloride using thionyl chloride, oxalyl chloride, or the like or making a mixed acid anhydride by making a base interact with mesyl chloride or the like, and then causing the resultant to interact with the phenol (or alcohol) derivative A-2 in the presence of a base. Alternatively, examples thereof include a method of directly esterifying A-1 and A-2 using a condensing agent such as carbodiimide.

As a method for producing the phenol (or alcohol) derivative A-2, it is possible to produce the phenol (or alcohol) derivative A-2, for example, by esterifying a carboxylic acid derivative A-3 using a compound A-4 in a case where Z is —COO—. X in the compound A-4 represents a hydroxy group or a leaving group. When X is a hydroxy group, it is possible to produce A-2 using a condensing agent such as carbodiimide or by dehydration condensation through heating in the presence of an acid catalysis. When X is a leaving group, it is possible to produce A-2 by heating A-3 and A-4 in the presence of a base in an aprotic polar solvent. It is possible to use a halogen, a mesyl group, a tosyl group, and the like as the leaving group.

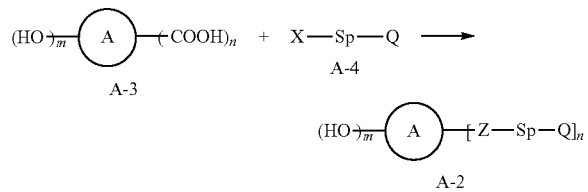

Since the polymerizable compound which is indicated by Formula (I) has low birefringence while exhibiting a liquid-crystalline property, it is possible to adjust the birefringence of a retardation film in a desired range by producing the retardation film using the polymerizable compound which is indicated by Formula (I). In particular, it is possible to obtain a reflection film with a narrow wavelength region of selective reflection, that is, a reflection film with high reflection wavelength region selectivity by forming a cholesteric liquid crystalline phase using the polymerizable compound which is indicated by Formula (I) and fixing the cholesteric liquid crystalline phase to a film.

In addition, since the absorption in a visible light region is extremely small regardless of the type of a substituent group of an aromatic ring or a linking group, the polymerizable compound which is indicated by Formula (I) satisfies a plurality of characteristics such as being colorless and transparent, having a wide liquid crystalline phase range, being easily dissolved in a solvent, or being easily polymerizable. By being derived therefrom, a cured film which is produced using a polymerizable composition which includes the polymerizable compound which is indicated by Formula (I) may satisfy a plurality of characteristics such as exhibiting sufficient hardness, being colorless and transparent, and having favorable weather resistance and heat resistance. Accordingly, it is possible to use the cured film which is formed using the polymerizable composition described above for various uses, for example, such as a retardation plate which is a constituent component of an optical element, a polarizer element, a selective reflection film, a color filter, an anti-reflection film, a view angle compensation film, a holographic, an alignment film, and the like.

<Polymerizable Composition>

In the polymerizable composition, only one type of the polymerizable compound which is indicated by Formula (I) may be included, and two or more types may be included.

The polymerizable compound which is indicated by Formula (I) (the total amount of two or more types in a case where two or more types are included) may be 5 mass % or more with respect to the solid content mass of the polymerizable composition, preferably 10 mass % to 85 mass %, more preferably 10 mass % to 75 mass %, and even more preferably 15 mass % to 70 mass %. However, the present invention is not limited to these ranges.

Other than the polymerizable compound which is indicated by Formula (I), the polymerizable composition may include other components such as other liquid crystal compounds, chiral compounds, polymerization initiators, and alignment controlling agents. Description will be given below of each component.

[Other Liquid Crystal Compounds]

The polymerizable composition may contain other one or more types of liquid-crystalline compounds which do not correspond to the polymerizable compound which is indicated by Formula (I) along with the polymerizable compound which is indicated by Formula (I). That is, the polymerizable composition may contain another one or more types of liquid-crystalline compounds other than the polymerizable compound which is indicated by Formula (I). Since the polymerizable compound which is indicated by Formula (I) has high compatibility with other liquid-crystalline compounds, loss of transparency and the like do not occur even when mixed with other liquid-crystalline compounds, and it is possible to form a film with high transparency. Since it is possible to use other liquid-crystalline compounds together therewith, it is possible to provide various compositions which are suitable for various uses. Examples of other liquid crystal compounds used together include a rod-like nematic liquid crystal compound. Examples of the rod-like nematic liquid crystal compound include azomethines, azoxys, cyanobiphenyls, cyanophenyl esters, benzoates, cyclohexane carboxylic acid phenyl esters, cyanophenyl cyclohexanes, cyano-substituted phenyl pyrimidines, alkoxy-substituted phenyl pyrimidines, phenyldioxanes, tolanes, and alkenyl cyclohexyl benzonitriles. It is possible to use not only a low molecular liquid crystal compound, but also a polymer liquid crystal compound.

Other liquid crystal compounds may be polymerizable or non-polymerizable. Various documents (for example, Y. Goto et al., Mol. Cryst. Liq. Cryst. 1995, Vol. 260, pp. 23 to 28) disclose a rod-like liquid crystal compound which does not have a polymerizable group.

It is possible to obtain the polymerizable rod-like liquid crystal compound by introducing a polymerizable group to a rod-like liquid crystal compound. Examples of the polymerizable group include an unsaturated polymerizable group, an epoxy group, and an aziridinyl group, and an unsaturated polymerizable group is preferable, and an ethylenically unsaturated polymerizable group is particularly preferable. It is possible to introduce a polymerizable group into the molecule of the rod-like liquid crystal compound with various methods. The number of polymerizable groups of the polymerizable rod-like liquid crystal compound is preferably 1 to 6, and more preferably 1 to 3. Examples of the polymerizable rod-like liquid crystal compound include the compounds which are described in Makromol. Chem., Vol. 190, page 2255 (in 1989), Advanced Materials Vol. 5, page 107 (in 1993), U.S. Pat. Nos. 4,683,327A, 5,622,648A, 5,770,107A, WO95/22586A, WO95/24455A, WO97/00600A, WO98/23580A, WO98/52905A, JP1989-272551A (JP-H1-272551A), JP1994-16616A (JP-H6-16616A), JP1995-110469A (JP-H7-110469A), JP1999-80081A (JP-H11-80081A), JP2001-328973A, and the like. Two or more types of polymerizable rod-like liquid crystal compounds may be used together. When two or more types of polymerizable rod-like liquid crystal compounds are used together, it is possible to reduce the alignment temperature.

The added amount of the other liquid crystal compounds is not particularly limited and is preferably 0 mass % to 85 mass % with respect to the solid content mass of the polymerizable composition, more preferably 0 mass % to 75 mass %, and even more preferably 0 mass % to 70 mass %. However, the added amount is not limited to these ranges. In the polymerizable composition, the mass ratio of the polymerizable compound which is indicated by Formula (I) and other liquid crystal compounds (mass of the polymerizable compound which is indicated by Formula (I)/mass of other liquid crystal compounds) may be 100/0 to 5/95 and the ratio described above is preferably 100/0 to 20/80 and more preferably 100/0 to 30/70. It is possible to adjust the ratio within the preferable ranges according to the use.

[Chiral Compound]

The polymerizable composition may include a chiral compound. Using a chiral compound makes it possible to prepare the polymerizable composition as a composition which exhibits a cholesteric liquid crystalline phase. The chiral compound may be liquid-crystalline or non-liquid-crystalline. It is possible to select the chiral compound from various chiral agents which are well known (for example, as described in the Liquid Crystal Device Handbook, Chapter 3 articles 4-3, TN, chiral agent for STN, page 199, Japan Society for the Promotion of Science No. 142 committee version, in 1989). The chiral compound generally includes an asymmetric carbon atom; however, it is also possible to use an axial asymmetric compound which does not include an asymmetric carbon atom or a planar asymmetric compound. Examples of the axial asymmetric compound or planar asymmetric compound include binaphthyl, helicene, paracyclophane, and derivatives thereof. The chiral compound (chiral agent) may have a polymerizable group. In a case where the chiral compound has a polymerizable group and the rod-like liquid crystal compound which is used therewith also has a polymerizable group, it is possible to form a polymer which has a repeating unit which is derived from the rod-like liquid crystal compound and a repeating unit which is derived from the chiral compound by polymerization reaction of the polymerizable chiral compound and the polymerizable rod-like liquid crystal compound. In this aspect, the polymerizable group which has the polymerizable chiral compound is preferably the same type of group as the polymerizable group of the polymerizable rod-like liquid crystal compound. Accordingly, the polymerizable group of the chiral compound is also preferably an unsaturated polymerizable group, an epoxy group, or an aziridinyl group, more preferably an unsaturated polymerizable group, and particularly preferably an ethylenically unsaturated polymerizable group.

In the polymerizable composition, the chiral compound is preferably 1 mol % to 30 mol % with respect to the polymerizable compound which is indicated by Formula (I). The usage amount of the chiral compound is preferably as small as possible since there is a tendency to not affect the liquid-crystalline property. Accordingly, the chiral compound is preferably a compound with a strong twisting force so as to be able to achieve a twisted alignment with a desired helical pitch even with a small amount thereof. Examples of chiral agents which exhibit a strong twisting force include the chiral agents described in JP2003-287623A. In addition, examples thereof include the chiral agents described in JP2002-302487A, JP2002-80478A, JP2002-80851A, and JP2014-034581A, LC-756 manufactured by BASF Corporation, and the like.

A film, which is formed by setting a polymerizable composition of an aspect which contains a chiral compound to a cholesteric liquid crystalline phase and then fixing the cholesteric liquid crystalline phase, exhibits selective reflection characteristics with respect to light with a predetermined wavelength according to the helical pitch and is useful as a reflection film (for example, a visible light reflection film or an infrared ray reflection film) By using the polymerizable compound which is indicated by Formula (I) which exhibits low birefringence, there is an advantage in that the reflection wavelength region is narrow and the selectivity is high compared to a film with the same thickness in which a liquid-crystalline compound with higher birefringence is used.

[Polymerization Initiator]

The polymerizable composition preferably contains a polymerization initiator. For example, in an aspect of forming a cured film by causing a curing reaction to proceed using ultraviolet ray irradiation, the polymerization initiator to be used is preferably a photopolymerization initiator which is able to initiate a polymerization reaction through ultraviolet ray irradiation. Examples of the photopolymerization initiator include the α-carbonyl compounds (described in each of the specifications of U.S. Pat. Nos. 2,367,661A and 2,367,670A), acyloin ether (described in the specification of U.S. Pat. No. 2,448,828A), the α-hydrocarbon-substituted aromatic acyloin compound (described in the specification of U.S. Pat. No. 2,722,512A), the polynuclear quinone compounds (described in the specifications of each of U.S. Pat. Nos. 3,046,127A and 2,951,758A), a combination of triarylimidazole dimer and p-aminophenyl ketone (described in the specification of U.S. Pat. No. 3,549,367A), acridine and phenazine compounds (described in the specifications of JP1985-105667A (JP-S60-105667A) and U.S. Pat. No. 4,239,850A), an oxadiazole compound (described in the specification of U.S. Pat. No. 4,212,970A), and the like.

The photopolymerization initiator is preferably included in the polymerizable composition at 0.1 mass % to 20 mass % with respect to the solid mass content of the polymerizable composition, and more preferably included at 1 mass % to 8 mass %.

[Alignment Controlling Agent]

An alignment controlling agent which contributes to the stable or quick formation of a liquid crystalline phase (for example, a cholesteric liquid crystalline phase) may be added to the polymerizable composition. Examples of the alignment controlling agent include a fluorine-containing (meth)acrylate-based polymer, the compounds which are represented by General Formulas (X1) to (X3) which are described in WO2011/162291A, and the compounds which are described in paragraphs [0020] to [0031] in JP2013-47204A. Two or more types selected therefrom may be contained. Regarding the compounds, it is possible to reduce or substantially horizontally align the tilt angle of the molecules of the liquid crystal compound at the air interface of the layer. Here, "horizontal alignment" in the present specification indicates that the long axis of the liquid crystal molecules and the film surface are parallel, but there is no strict demand for the horizontal alignment to be parallel and, in the present specification, horizontal alignment has the meaning of an alignment at which an inclined angle made with a horizontal surface is less than 20 degrees. In a case where the liquid crystal compound is horizontally aligned in the vicinity of the air interface, the transparency in the visible light region is high since alignment defects are not easily generated. On the other hand, when the molecules of the liquid crystal compound are aligned at a large tilt angle, for example, in a case of making a cholesteric liquid crystalline phase, since the helical axis is shifted from the film surface normal line, the reflection ratio is decreased, finger print patterns are generated, or increases in haze or diffraction are exhibited, which is not preferable.

Examples of a fluorine-containing (meth)acrylate-based polymer which is able to be used as an alignment controlling agent are described in [0018] to [0043] in JP2007-272185A and the like.

As the alignment controlling agent, one type of compound may be used individually or two or more types of compound may be used together.

The content of the alignment controlling agent in the polymerizable composition is preferably 0.01 mass % to 10 mass % of the mass of the compound of Formula (I), more preferably 0.01 mass % to 5 mass %, and particularly preferably 0.02 mass % to 1 mass %.

[Cross-linking Agent]

The polymerizable composition may arbitrarily contain a cross-linking agent for film strength improvement and durability improvement after curing. It is possible to favorably use a cross-linking agent which is cured by ultraviolet rays, heat, moisture, or the like.

The cross-linking agent is not particularly limited and it is possible to appropriately select the cross-linking agent according to the purpose and examples thereof include polyfunctional acrylate compounds such as trimethylol propane tri(meth)acrylate, pentaerythritol tri(meth)acrylate, and pentaerythritol tetraacrylate; epoxy compounds such as glycidyl (meth)acrylate and ethylene glycol diglycidyl ether; aziridine compounds such as 2,2-bishydroxymethyl butanoltris[3-(1-aziridinyl) propionate] and 4,4-bis(ethyleneimino carbonyl amino) diphenyl methane; isocyanate compounds such as hexamethylene diisocyanate and biuret type isocyanate; a polyoxazoline compound which has an oxazoline group in a side chain; alkoxy silane compounds such as vinyl trimethoxy silane and N-(2-aminoethyl)3-amino propyl trimethoxy silane, and the like. In addition, it is possible to use a well-known catalyst according to the reactivity of the cross-linking agent and to improve the productivity in addition to the film strength and durability improvement. One type thereof may be used individually or two or more types may be used together.

The content of the cross-linking agent is preferably 3 mass % to 20 mass % with respect to the solid content mass of the polymerizable composition, and more preferably 5 mass % to 15 mass %. The effects of the cross-linking density improvement are high when the content of the cross-linking agent is 3 mass % or more and the stability of the cholesteric liquid crystal layer is higher when the content of the cross-linking agent is 20 mass % or less.

[Other Additive Agents]

The polymerizable composition may contain one type or two or more types of other additive agents such as an anti-oxidant, an ultraviolet absorbent, a sensitizer, a stabilizer, a plasticizer, a chain transfer agent, a polymerization inhibitor, an anti-foaming agent, a levelling agent, a thickener, a flame retardant, surfactants, a dispersing agent, a dye, and coloring materials such as pigments.

<Film>

The polymerizable compound which is indicated by Formula (I) is useful as the material of various optical films such as a retardation film and a reflection film and it is possible to form various optical films using a polymerizable composition which includes the polymerizable compound which is indicated by Formula (I).

[Method for Producing Film]

One example of a method for producing an optical film is a production method which includes at least (i) coating a surface of a substrate or the like with the polymerizable composition which includes the polymerizable compound which is indicated by Formula (I) and setting the polymerizable composition to a liquid crystalline phase state (a cholesteric liquid crystalline phase or the like) and (ii) forming a cured film by causing a curing reaction of the composition described above to proceed and fixing the liquid crystalline phase.

It is also possible to produce a film in which a plurality of cured films are laminated by repeating the steps of (i) and (ii) a plurality of times. In addition, it is also possible to produce a film in which a plurality of cured films are laminated by adhering a plurality of cured films using an adhesive.

In the step (i) described above, firstly, a substrate or the surface of an alignment film which is formed thereon is coated with a polymerizable composition. The polymerizable composition is preferably prepared as a coating liquid in which a material is dissolved and/or dispersed in a solvent. An organic solvent is preferably used as the solvent which is used for preparation of the coating liquid. Examples of the organic solvent include amide (for example, N,N-dimethyl formamide); sulfoxide (for example, dimethyl sulfoxide); a hetero ring compound (for example, pyridine); hydrocarbon (for example, benzene and hexane); alkyl halide (for example, chloroform and dichloro methane); ester (for example, methyl acetate and butyl acetate); ketone (for example, acetone and methylethyl ketone); ether (for example, tetrahydrofuran and 1,2-dimethoxy ethane); 1,4-butanediol diacetate, and the like. Among these, alkyl halide and ketone are particularly preferable. Two or more types of organic solvents may be used together.

It is possible to apply a coating liquid using various methods such as a wire bar coating method, an extrusion coating method, a direct gravure coating method, a reverse gravure coating method, and a dye coating method. In addition, it is also possible to form a coated film by discharging a composition from nozzles using an inkjet apparatus.

Next, a polymerizable composition which is a coated film coated on a surface is set to a state of a liquid crystalline phase such as a cholesteric liquid crystalline phase. In an aspect in which the polymerizable composition is prepared as a coating liquid which includes a solvent, there are cases where it is possible to set the liquid crystalline phase state by drying the coated film and removing the solvent. In addition, the coated film may be heated as desired to reach the temperature for transition to the liquid crystalline phase. For example, it is possible to stably set the liquid crystalline phase state by temporarily heating to the isotropic phase temperature and then cooling to the liquid crystalline phase transition temperature. The liquid crystalline phase transition temperature of the polymerizable composition is preferably within a range of 10° C. to 250° C. in terms of the production suitability or the like, and more preferably within a range of 10° C. to 150° C. When the temperature is less than 10° C., there are cases where a cooling step or the like is necessary in order to decrease the temperature to a temperature range in which a liquid crystalline phase is exhibited. In addition, when the temperature exceeds 250° C., a high temperature is necessary in order to temporarily set an isotropic liquid state at a higher temperature than the temperature range in which a liquid crystalline phase is exhibited and there may be disadvantages in terms of wasting heat energy, deforming the substrate, degeneration, or the like.

Next, in step (ii), the coated film which is in a state of a liquid crystalline phase is cured. The curing may proceed according to any one of the polymerization methods such as a radical polymerization method, an anion polymerization method, a cation polymerization method, and an coordination polymerization method. A suitable polymerization method may be selected according to the polymerizable compound which is indicated by Formula (I). A polymer which has a unit which is derived from the polymerizable compound which is indicated by Formula (I) in the constituent units is obtained by the polymerization.

In one example, the curing reaction is made to proceed through the irradiation with ultraviolet rays. A light source such as an ultraviolet lamp is used for the ultraviolet ray irradiation. In this step, the curing reaction of the composition described above is made to proceed by the irradiation with ultraviolet rays, a cholesteric liquid crystalline phase is fixed, and a cured film is formed.

The irradiation energy amount of the ultraviolet rays is not particularly limited; however, in general, approximately 0.1 J/cm$^2$ to 0.8 J/cm$^2$ is preferable. In addition, the time for irradiating the coated film with ultraviolet rays is not particularly limited and may be determined from the points of view of both the sufficient strength and productivity of the cured film.

In order to promote the curing reaction, the ultraviolet ray irradiation may be carried out while heating. In addition, the temperature during the ultraviolet ray irradiation is preferably maintained in a temperature range in which a liquid crystalline phase is exhibited so as not to disturb the liquid crystalline phase. In addition, since the oxygen concentration in the atmosphere contributes to the degree of polymerization, in a case where the desired polymerization degree is not reached in air and the film strength is not sufficient, the oxygen concentration in the atmosphere is preferably reduced by a method such as nitrogen substitution.

In the step described above, the liquid crystalline phase is fixed and a cured film is formed. Here, regarding the "fixed" liquid crystalline phase state, a state in which the alignment of the compound which is a liquid crystalline phase is maintained is the most typical and is a preferable aspect thereof. Without only being limited thereto, in detail, the "fixed" liquid crystalline phase state has the meaning of a state in which there is no fluidity in the layer in a temperature range of generally 0° C. to 50° C., or under more severe conditions of −30° C. to 70° C. and moreover, in which it is possible to continue to stably keep the form of the alignment fixed without changes in the form of the alignment being generated by an external field or external force. In the present invention, the alignment state of the liquid crystalline phase is preferably fixed by the curing reaction which proceeds due to the ultraviolet ray irradiation.

Here, in the film, it is sufficient if the optical characteristics of the liquid crystalline phase are maintained in a layer and it is no longer necessary for the composition in the cured film to exhibit the liquid-crystalline property at the end. For example, the composition may be polymerized by the curing reaction and lose the liquid-crystalline property.

The thickness of the cured film is not particularly limited. A preferable film thickness may be determined according to the use or according to the desired optical characteristics. In general, the thickness is preferably 0.05 μm to 50 μm and more preferably 1 μm to 35 μm.

[Substrate]

The film may have a substrate. As long as the substrate has a self-supporting property and supports the cured film, the material and optical characteristics are not limited. It is possible to select from a glass plate, a quartz plate, a polymer film, and the like. A substrate which has high transparency with respect to ultraviolet light may be used according to the use. Examples of the polymer film which has high transmittance with respect to visible light include a polymer film for various optical films which is used as members of a display apparatus such as a liquid crystal display device. Examples of the substrate include polyester films such as polyethylene terephthalate (PET), polybutylene terephthalate, and polyethylene naphthalate (PEN); polycarbonate (PC) films, polymethyl methacrylate films; polyolefin films such as polyethylene and polypropylene; polyimide films, triacetyl cellulose (TAC) films, and the like. Polyethylene terephthalate films and triacetyl cellulose films are preferable.

[Alignment Layer]

The film may have an alignment layer between a substrate and a cured film. The alignment layer has a function which more precisely regulates the alignment direction of the liquid crystal compound. It is possible to provide the alignment layer using a means such as a rubbing treatment of an organic compound (preferably a polymer), oblique vapor deposition of an inorganic compound, or formation of a layer which has microgrooves. Furthermore, an alignment layer which has an alignment function by applying an electric field, applying a magnetic field, or by light irradiation is also known. The alignment layer is preferably formed on the surface of a polymer film by a rubbing treatment.

The material which is used for the alignment layer is preferably a polymer of an organic compound and a polymer which is itself able to be cross-linked or a polymer which is cross-linked by a cross-linking agent is frequently used. Naturally, a polymer which has both functions is also used. Examples of the polymer include polymethyl methacrylate, an acrylic acid/methacrylic acid copolymer, a styrene/maleinimide copolymer, polyvinyl alcohol and modified polyvinyl alcohol, poly(N-methylol acrylamide), a styrene/vinyl toluene copolymer, chlorosulfonated polyethylene, nitro cellulose, polyvinyl chloride, chlorinated polyolefin, polyester, polyimide, a vinyl acetate/vinyl chloride copolymer, an ethylene/vinyl acetate copolymer, carboxymethyl cellulose, gelatin, polymers such as polyethylene, polypropylene, and polycarbonate, compounds such as a silane coupling agent, and the like. Examples of a preferable polymer include water-soluble polymers such as poly(N-methylol acrylamide), carboxymethyl cellulose, gelatin, polyvinyl alcohol, and modified polyvinyl alcohol and, among these, gelatin, polyvinyl alcohol, and modified polyvinyl alcohol are preferable, and polyvinyl alcohol and modified polyvinyl alcohol are particularly preferable.

[Adhesive Layer]

In a case of adhering a plurality of cured films using an adhesive, an adhesive layer is provided between the cured films. The adhesive layer may be formed from the adhesive.

As the adhesive, from the point of view of the curing method, there are hot melt type adhesives, heat curing type adhesives, photocuring type adhesives, reaction curing type adhesives, and pressure sensitive adhesive type adhesives which does not need curing, and it is possible to use compounds such as an acrylate-based compound, a urethane-based compound, a urethane acrylate-based compound, an epoxy-based compound, an epoxy acrylate-based compound, a polyolefin-based compound, a modified olefin-based compound, a polypropylene-based compound, an ethylene vinyl alcohol-based compound, a vinyl chloride-based compound, a chloroprene rubber-based compound, a cyano acrylate-based compound, a polyamide-based compound, a polyimide-based compound, a polystyrene-based compound, a polyvinyl butyral-based compound, and the like as the material for each of the adhesives. A photocuring type is preferable as the curing method from the point of view of the workability and productivity, and an acrylate-based compound, a urethane acrylate-based compound, an epoxy acrylate-based compound, and the like are preferably used as the material from the point of view of the optical transparency and the heat resistance.

The film thickness of the adhesive layer is 0.5 μm to 10 μm and preferably 1 μm to 5 μm. In a case of use as a half mirror for displaying a projection image, it is preferable to provide an even film thickness in order to reduce color variation or the like.

[Use of Film]

An aspect of the film is a film in which the alignment (for example, horizontal alignment, vertical alignment, hybrid alignment, and the like) of the liquid crystalline phase of the polymerizable composition is fixed and a film which exhibits optical anisotropy. The film is used as an optical compensation film or the like of a liquid crystal display device or the like.

An aspect of the optical film is a film which includes a layer in which the cholesteric liquid crystalline phase of the polymerizable composition is fixed and a film which exhibits selective reflection characteristics with respect to a light of a predetermined wavelength region. Liquid crystal molecules are arranged in a helical form in the cholesteric liquid crystalline phase. The layer in which a cholesteric liquid crystalline phase is fixed (may be referred to below as a "cholesteric liquid crystal layer") selectively reflects any one of right circular polarization and left circular polarization in the selective reflection wavelength region and functions as a circular polarization selective reflection layer which transmits circular polarization of the other sense. It is possible to use a film which includes one cholesteric liquid crystal layer or two or more cholesteric liquid crystal layers for various uses. In the film which includes two or more cholesteric liquid crystal layers, the sense of the circular polarization which each of the cholesteric liquid crystal layers reflects may be the same or opposite according to the use. In addition, the center wavelength of the selective reflection of each of the cholesteric liquid crystal layers which will be described below may also be the same or different according to the use.

Here, in the present specification, "sense" regarding the circular polarization has the meaning of whether the circular polarization is right circular polarization or left circular polarization. The sense of circular polarization is defined thus: in a case of viewing light proceeding toward the front, a case where the front end of the electric field vector rotates clockwise as time passes is right circular polarization and a case where the front end of the electric field vector rotates counterclockwise is left circular polarization. In the present specification, the technical term "sense" may be used regarding the helical twisted direction of the cholesteric liquid crystal. The selective reflection by the cholesteric liquid crystal reflects right circular polarization and transmits left circular polarization in a case where the helical twisted direction (sense) of the cholesteric liquid crystal is to the right and reflects left circular polarization and transmits right circular polarization in a case where the sense is to the left.

For example, it is possible to use a film which includes a cholesteric liquid crystal layer which exhibits selective reflection characteristics in the visible light wavelength region (wavelength of 400 nm to 750 nm) as a screen or half mirror for displaying a projection image. In addition, by controlling the reflection band, it is possible to use the film as a color filter or a filter (for example, refer to JP2003-294948A) which improves the color purity of display light of a display.

In addition, it is possible to use the optical film for various uses such as a polarizer, a reflection film, an anti-reflection film, a view angle compensation film, a holographic, an alignment film, or the like, that are constituent components of an optical element.

Description will be given below of a use as a member for displaying a projection image which is a particularly preferable use.

[Member for Displaying Projection Image]

Through the above function of the cholesteric liquid crystal layer, it is possible to form a projection image by reflecting circular polarization of any one of the senses in a wavelength which exhibits selective reflection in the incident light. The projection image may be displayed on the surface of a member for displaying a projection image and viewed in this manner or may be a virtual image which is seen to float up in front of the member for displaying a projection image as viewed from the observer.

The center wavelength λ of selective reflection depends on a pitch P (=the cycle of the helix) with a helical structure in a cholesteric phase and follows a relationship of λ=n×P with an average refractive index n of the cholesteric liquid crystal layer. Here, the center wavelength λ of the selective reflection of the cholesteric liquid crystal layer has the meaning of a wavelength which is at the center of gravity of the reflection peak of the circular polarization reflection spectrum which is measured from the normal direction of the cholesteric liquid crystal layer. As understood from the formula described above, it is possible to adjust the center wavelength of the selective reflection by adjusting the pitch of the helical structure. That is, by adjusting the n Value and the P value, for example, it is possible to adjust the center wavelength λ and make the center wavelength of the apparent selective reflection a wavelength region of 450 nm to 495 nm in order to selectively reflect any one of right circular polarization and left circular polarization with respect to blue light. Here, the center wavelength of the apparent selective reflection has the meaning of a wavelength which is at the center of gravity of the reflection peak of the circular polarization reflection spectrum of the cholesteric liquid crystal layer which is measured from the observation direction during use (when being used as a member for displaying a projection image). Since the pitch of the cholesteric liquid crystalline phase depends on the type of the chiral agent which is used along with the polymerizable liquid crystal compound or the added density thereof, it is possible to obtain a desired pitch by adjusting these. Here, regarding the method for measuring the sense or the pitch of the helix, it is possible to use the method described on page 46 of "Liquid Crystal Chemical Experiment Introduction" Japan Liquid Crystal Society published by Sigma Corporation in 2007, and page 196 of "Liquid Crystal Handbook" Liquid Crystal Handbook Editing Committee, Maruzen.

Regarding the half-value width $\Delta\lambda$ (nm) of the selective reflection wavelength region which exhibits circular polarization selective reflection, $\Delta\lambda$ depends on the birefringence $\Delta n$ of the liquid crystal compound and the pitch P and follows a relationship of $\Delta\lambda = \Delta n \times P$. Therefore, it is possible to control the width of the selective reflection wavelength region by adjusting $\Delta n$. That is, in a cholesteric liquid crystal layer which is formed from a composition which includes the polymerizable liquid crystal compound of the present invention with low birefringence, it is possible to increase the wavelength selectivity of the selective reflection.

As an index which indicates the wavelength selectivity of the selective reflection, for example, it is possible to use $\Delta\lambda/\lambda$ which is a ratio of the half-value width $\Delta\lambda$ of the selective reflection wavelength region and the center wavelength $\lambda$ of the selective reflection. Regarding the film of the present invention, specifically the film which is used as a member for displaying a projection image, $\Delta\lambda/\lambda$ is preferably 0.09 or less and more preferably 0.07 or less. In more detail, in a cholesteric liquid crystal layer in a film, $\Delta\lambda/\lambda$ preferably satisfies the above and, in a film which includes two or more cholesteric liquid crystal layers, $\Delta\lambda/\lambda$ preferably satisfies the above in each of the two or more cholesteric liquid crystal layers. Here, in each of the layers, $\Delta\lambda$ and $\lambda$ may be each the same as or different from each other.

It is possible to produce a member for displaying a projection image which is able to display a full color projection image by producing each cured film having a center wavelength of apparent selective reflection in each of a red light wavelength region, a green light wavelength region, and a blue light wavelength region and laminating these using the polymerizable composition described above. In detail, the half mirrors are each in ranges of 750 nm to 620 nm, 630 nm to 500 nm, and 530 nm to 420 nm and the cured films each having a center wavelength of the selective reflection different from each other (for example, 50 nm or more different) are preferably laminated.

It is possible to display a clear projection image with good light use efficiency by adjusting the center wavelength of selective reflection of each cured film according to the light emitting wavelength region of the light source which is used for projection and the use form of the member for displaying a projection image. In particular, it is possible to display a clear color projection image with good light use efficiency by adjusting each center wavelength of the selective reflection of the cured film according to each light emitting wavelength region of the light source which is used for projection and the like. Examples of the use of the member for displaying a projection image specifically include a use for the incidence angle of projected light onto the surface of a half mirror for displaying a projection image, a use for the projection image observation direction on the surface of a member for displaying a projection image, and the like.

For example, it is possible to make a half mirror which is able to be used as a combiner of a head up display by making a member for displaying a projection image with a configuration which has transmittance with respect to light in the visible light region. The half mirror for displaying a projection image is able to visually display an image which is projected from a projector or the like and, when the half mirror for displaying a projection image is observed from the same surface side on which the image described above is displayed, it is possible to observe information or scenery on the opposite surface side at the same time.

When used as a half mirror for displaying a projection image, the cured film which is produced as described above, specifically, a laminate of three or more cured films, is preferably provided on a substrate surface. The substrate is preferably transparent in the visible light region with low birefringence. Examples of the substrate include inorganic glass or polymer resins (acryl resins (acrylic acid esters such as polymethyl (meth)acrylate), polycarbonate, cyclic polyolefins such as cyclopentadiene-based polyolefins and norbornene-based polyolefins, polyolefins such as polypropylene, aromatic vinyl polymers such as polystyrene, polyarylate, cellulose acylate, and the like).

The half mirror for displaying a projection image may include an anti-reflection layer. The anti-reflection layer is preferably included on the uppermost surface. The anti-reflection layer may be provided on the uppermost surface which is on the viewing side when using the half mirror for displaying a projection image and may be provided on the uppermost surface on the opposite side, but is preferably provided on the uppermost surface on the viewing side. In a case of providing the cured film on the substrate surface, the anti-reflection layers may be provided on both the surface on the substrate side and the cured film side which is on the viewing side. This is because this configuration makes it hard for double images which may occur particularly in a case where the birefringence of the substrate is high to occur.

Other than films formed with a fine surface roughness, examples of anti-reflection layers include a layer with a configuration of a two-layer film in which a high refractive index film and a low refractive index film are combined, a layer with a three-layer film configuration where an intermediate refractive index film, a high refractive index film, and a low refractive index film are laminated in order, and the like.

Example configurations include a configuration with two layers of a layer of high refractive index and a layer of low refractive index in order from the lower side, a configuration where three layers with different refractive indices are laminated in order, the three layers being a layer of intermediate refractive index (the refractive index is higher than the underlayer and the refractive index is lower than the layer of high refractive index), a layer of high refractive index, and a layer of low refractive index, and the like, and, moreover, a configuration where many anti-reflection layers are laminated has been also proposed. Among these, in terms of the durability, optical characteristics, cost, productivity, and the like, it is preferable to have a layer of intermediate refractive index, a layer of high refractive index, and a layer of low refractive index in this order on a hard coat layer and examples thereof include the configurations described in JP1996-122504A (JP-H8-122504A), JP1996-110401A (JP-H8-110401A), JP1998-300902A (JP-H10-300902A), JP2002-243906A, JP2000-111706A, and the like. In addition, an anti-reflection film with a three-layer configuration with excellent robustness with respect to changes in the film thickness is described in JP2008-262187A. In a case of installing the anti-reflection film with a three-layer configuration described above on the surface of an image display apparatus, it is possible to make the average value of the reflection rate 0.5% or less, it is possible to remarkably reduce glare, and it is possible to obtain an image with excellent solidity. In addition, another function may be added to each layer and examples thereof include a layer of low refractive index with an anti-fouling property, a layer of high refractive index with an anti-static property, a hard coat layer with anti-static property, a hard coat layer with an anti-glare characteristic (for example, JP1998-206603A (JP-H10-206603A), JP2002-243906A, JP2007-264113A, and the like), and the like.

Examples of the inorganic material which forms the anti-reflection layer include $SiO_2$, SiO, $ZrO_2$, $TiO_2$, TiO, $Ti_2O_3$, $Ti_2O_5$, $Al_2O_3$, $Ta_2O_5$, $CeO_2$, MgO, $Y_2O_3$, $SnO_2$, $MgF_2$, $WO_3$, and the like and it is possible to use these individually or as two or more types together. Among these, $SiO_2$, $ZrO_2$, $TiO_2$, and $Ta_2O_5$ are preferable since vacuum vapor deposition is possible at low temperatures and it is also possible to form a film on the surface of a plastic substrate.

Examples of a multilayer film which is formed by inorganic material include a laminated structure in which a high refractive index material layer and a low refractive index material layer are alternately formed into a film where the total optical film thickness of a $ZrO_2$ layer and a $SiO_2$ layer is λ/4, the optical film thickness of a $ZrO_2$ layer is λ/4, and the optical film thickness of a $SiO_2$ layer of a uppermost layer is λ/4 from the substrate side. Here, λ is the designed wavelength and 520 nm is generally used. The uppermost layer is preferably $SiO_2$ since the refractive index is low and it is possible to impart mechanical strength to the anti-reflection layer.

In a case of forming the anti-reflection layer using an inorganic material, it is possible to adopt, for example, a vacuum vapor deposition method, an ion plating method, a sputtering method, a CVD method, a method for precipitating by a chemical reaction in a saturated solution, or the like for the film-forming method.

Examples of the organic material which is used for the layer of low refractive index include a tetrafluoroethylene-hexafluoropropylene copolymer (FFP), polytetrafluoroethylene (PTFE), an ethylene-tetrafluoroethylene copolymer (ETFE), and the like and, moreover, it is possible to favorably use the composition which contains a fluorine-containing curable resin and inorganic fine particles which is described in JP2007-298974A, or the hollow silica particle-containing low refractive index coating compositions described in JP2002-317152A, JP2003-202406A, and JP2003-292831A. Regarding the film-forming method, it is possible to carry out the film-forming using a coating method with excellent mass productivity such as a spin coating method, a dip coating method, or a gravure coating method, other than a vacuum vapor deposition method.

Regarding the layer of low refractive index, the refractive index is preferably 1.30 to 1.51. 1.30 to 1.46 is more preferable and 1.32 to 1.38 is even more preferable.

Examples of the organic material which is used for the layer of intermediate refractive index and the layer of high refractive index include inorganic particles which have a binder which is obtained by cross-linking or by a polymerization reaction of an ionizing radiation curable compound which includes an aromatic ring, an ionizing radiation curable compound which includes a halogenated element other than fluorine (for example, Br, I, Cl, and the like), an ionizing radiation curable compound which includes an atom such as S, N, and P, and the like, and $TiO_2$ which is added to the binder as main components. In detail, examples thereof include those described in paragraph numbers [0074] to [0094] in JP2008-262187A.

The refractive index of the layer of high refractive index is preferably 1.65 to 2.20 and more preferably 1.70 to 1.80. The refractive index of the layer of intermediate refractive index is adjusted so as to be a value between the refractive index of the layer of low refractive index and the refractive index of the layer of high refractive index. The refractive index of the layer of intermediate refractive index is preferably 1.55 to 1.65 and more preferably 1.58 to 1.63.

The film thickness of the anti-reflection layer is not particularly limited; however, approximately 0.1 μm to 10 μm, 1 μm to 5 μm, or 2 μm to 4 μm are sufficient.

EXAMPLES

More detailed description will be given below of the features of the present invention using Examples and Comparative Examples. It is possible to appropriately change the materials, the usage amounts, the ratios, the process content, the process order, and the like which are shown in the Examples below within a scope which does not depart from the spirit of the invention. Therefore, the range of the present invention is not to be interpreted as limited by the specific examples which will be shown below.

<Synthesis Examples of Polymerizable Compound Indicated by Formula (I)
(Compound 1)

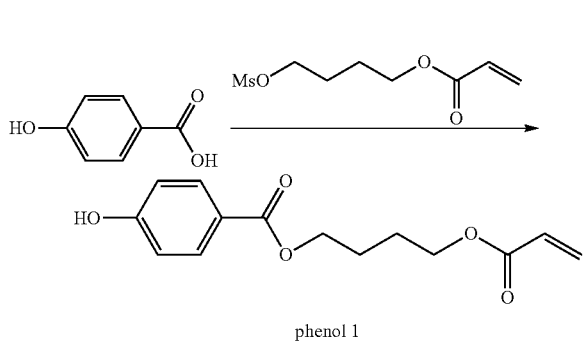

phenol 1

Para-hydroxybenzoic acid (9.0 g) was stirred in dimethylacetamide (70 mL), triethylamine (9.8 mL), 4-acryloyloxy butyl methanesulfonate (11.1 g), and dibutylhydroxytoluene (BHT, 0.2 g) were added thereto, and stirring was carried out for 10 hours at an inner temperature of 70° C. After cooling the resultant to 30° C., water and ethyl acetate were added, a water layer was removed, and cleansing was carried out using saturated sodium bicarbonate water, dilute hydrochloric acid, and a saline solution in this order. After an organic layer was dried using magnesium sulfate and the drying agent was filtered, reduced pressure distillation was carried out on the solvent after adding BHT (0.1 g), and a phenol derivative 1 was obtained.

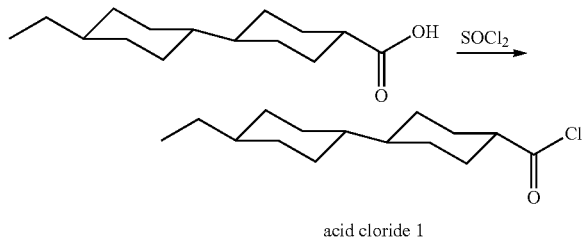

acid cloride 1

Next, 4-ethylcyclohexyl-4-cyclohexyl carboxylic acid (31 g) was heated to 60° C. after adding toluene (40 mL) and dimethyl formamide (0.3 mL) thereto, thionyl chloride (18 g) was added dropwise thereto, and stirring was carried out for 3 hours at an inner temperature of 60° C. After that, reduced pressure distillation was carried out on the solvent and a carboxylic acid chloride derivative 1 (33 g) was obtained.

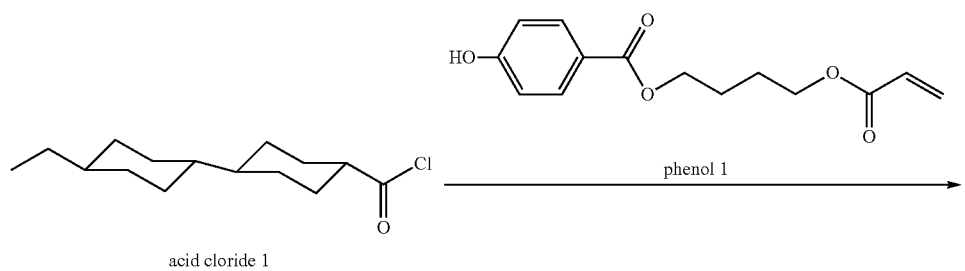

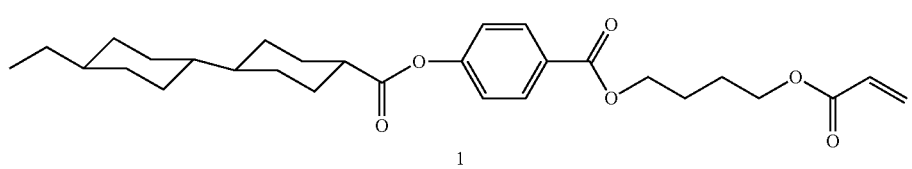

The phenol derivative 1 (11.9 g) was stirred in 70 mL of tetrahydrofuran, and dimethylaminopyridine (0.3 g) and the carboxylic acid chloride derivative 1 (12.7 g) were added thereto. The reaction liquid was cooled until the inner temperature became 0° C., triethylamine (7.6 mL) was added dropwise thereto, stirring was carried out for 2 hours at 25° C., and further stirring was carried out for 30 minutes after adding methanol (20 mL). After water and ethyl acetate were added, a water layer was removed, and cleansing was carried out using saturated sodium bicarbonate water, dilute hydrochloric acid, and a saline solution in this order, the organic layer was dried using magnesium sulfate and the drying agent was filtered. 10 g of a compound 1 was obtained by carrying out reduced pressure distillation on the solvent after adding BHT (0.1 g), adding methanol (80 mL), carrying out cooling until the inner temperature became 0° C., carrying out stirring for 3 hours, and filtering the generated crystals.

H-NMR (solvent: CDCl$_3$) δ (ppm):
0.8-1.3 (m, 14H), 1.5-1.6 (m, 2H), 1.7-1.9 (m, 10H), 2.1-2.2 (m, 2H), 2.4-2.5 (m, 1H), 4.2 (t, 2H), 4.4 (t, 2H), 5.8 (dd, 1H), 6.1 (dd, 1H), 6.4 (dd, 1H), 7.1 (d, 2H), 8.1 (d, 2H)
(Compound 2)

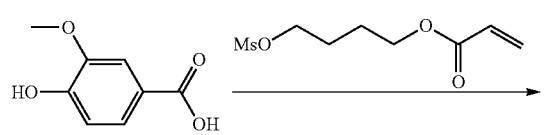

-continued

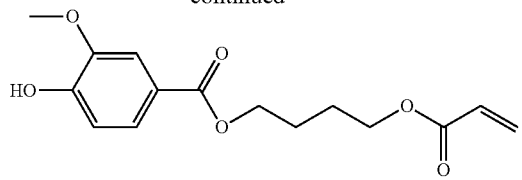

Vanillic acid (10.9 g) was stirred in dimethylacetamide (70 mL), triethylamine (9.8 mL), 4-acryloyloxy butyl methanesulfonate (11.1 g), and BHT (0.2 g) were added thereto, and stirring was carried out for 10 hours at an inner temperature of 70° C. After cooling the resultant to 30° C., water and ethyl acetate were added, a water layer was removed, and cleansing was carried out using saturated sodium bicarbonate water, dilute hydrochloric acid, and a saline solution in this order. After an organic layer was dried using magnesium sulfate and the drying agent was filtered, reduced pressure distillation was carried out on the solvent after adding BHT (0.1 g) thereto, and a phenol derivative 2 was obtained.

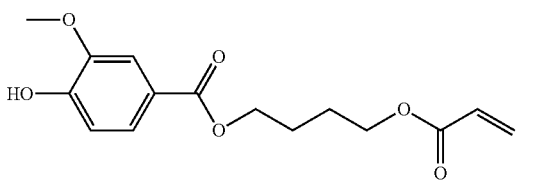

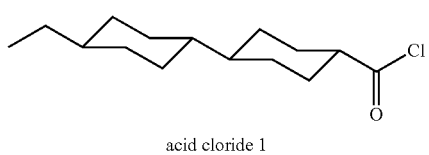

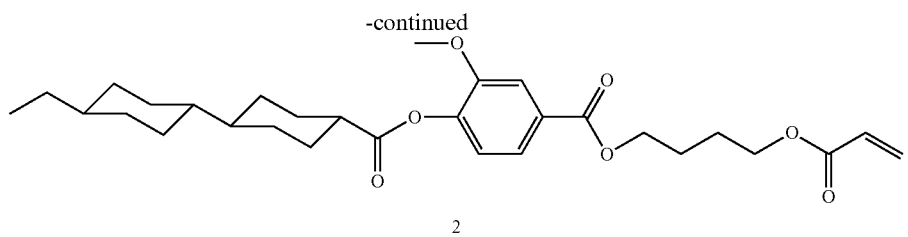

2

The phenol derivative 2 (13.1 g) was stirred in 70 mL of tetrahydrofuran, and dimethylaminopyridine (0.3 g) and the carboxylic acid chloride derivative 1 (12.7 g) were added thereto. The reaction liquid was cooled until the inner temperature became 0° C., triethylamine (7.6 mL) was added dropwise thereto, stirring was carried out for 2 hours at 25° C., and further stirring was carried out for 30 minutes after adding methanol (20 mL) thereto. After water and ethyl acetate were added thereto, a water layer was removed, and cleansing was carried out using saturated sodium bicarbonate water, dilute hydrochloric acid, and a saline solution in this order, the organic layer was dried using magnesium sulfate and the drying agent was filtered. 13 g of a compound 2 was obtained by carrying out reduced pressure distillation on the solvent after adding BHT (0.1 g) thereto, adding methanol (80 mL) thereto, carrying out cooling until the inner temperature became 0° C., carrying out stirring for 3 hours, and filtering the generated crystals.

H-NMR (solvent: CDCl$_3$) δ (ppm):
0.8-1.3 (m, 14H), 1.5-1.6 (m, 2H), 1.7-1.9 (m, 10H), 2.1-2.2 (m, 2H), 2.5-2.6 (m, 1H), 3.9 (s, 3H), 4.2 (t, 2H), 4.4 (t, 2H), 5.8 (dd, 1H), 6.1 (dd, 1H), 6.4 (dd, 1H), 7.0 (d, 1H), 7.6-7.7 (m, 2H)

(Compound 32)

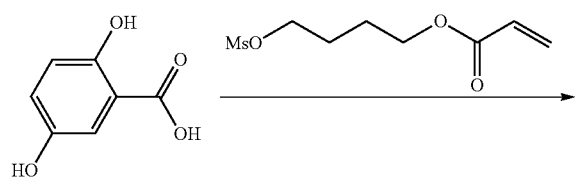

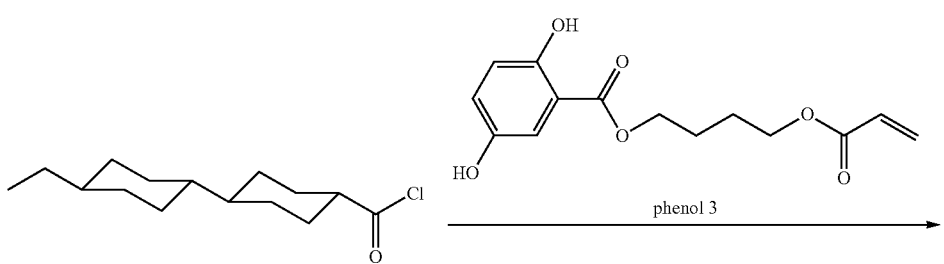

phenol 3

2,5-Dihydroxybenzoic acid (10 g) was stirred in dimethylacetamide (50 mL), triethylamine (9.8 mL), 4-acryloyloxy butyl methanesulfonate (11.1 g), and BHT (0.2 g) were added thereto, and stirring was carried out for 10 hours at an inner temperature of 70° C. After cooling the resultant to 30° C., water and ethyl acetate were added thereto, a water layer was removed, and cleansing was carried out using saturated sodium bicarbonate water, dilute hydrochloric acid, and a saline solution in this order. After an organic layer was dried using magnesium sulfate and a drying agent was filtered, reduced pressure distillation was carried out on the solvent after adding BHT (0.1 g), and a phenol derivative 3 was obtained.

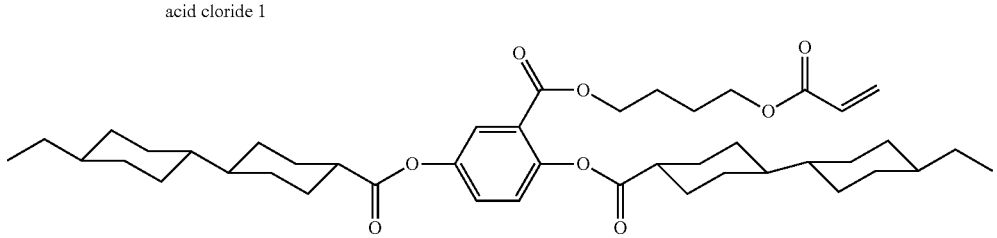

32

The phenol derivative 3 (3.2 g) was stirred in 16 mL of tetrahydrofuran, and dimethylaminopyridine (0.1 g) and the carboxylic acid chloride derivative 1 (6.3 g) were added thereto. The reaction liquid was cooled until the inner temperature became 0° C., triethylamine (3.6 mL) was added dropwise thereto, stirring was carried out for 3 hours at 25° C., and further stirring was carried out for 30 minutes after adding methanol (30 mL) and water (15 mL) thereto. Cooling was carried out until the inner temperature became 0° C., stirring was carried out for 3 hours, and the generated crystals were filtered. 8.5 g of a compound 32 was obtained by stirring the crystals in water (10 mL) and methanol (50 mL) for 30 minutes and carrying out filtering.

H-NMR (solvent: CDCl$_3$) δ (ppm):

0.8-1.3 (m, 28H), 1.4-1.6 (m, 4H), 1.7-1.9 (m, 16H), 2.1-2.3 (m, 4H), 2.4-2.6 (m, 2H), 4.2 (t, 2H), 4.3 (t, 2H), 5.8 (dd, 1H), 6.1 (dd, 1H), 6.4 (dd, 1H), 7.0 (d, 1H), 7.2 (dd, 1H), 7.6 (d, 1H)

(Compound 42)

The phenol derivative 3 (3.3 g) was stirred in 16 mL of tetrahydrofuran, and dimethylaminopyridine (0.1 g) and the carboxylic acid chloride derivative 2 (6.6 g) were added thereto. The reaction liquid was cooled until the inner temperature became 0° C., triethylamine (3.6 mL) was added dropwise thereto, stirring was carried out for 3 hours at 25° C., and further stirring was carried out for 30 minutes after adding methanol (30 mL) and water (15 mL) thereto. Cooling was carried out until the inner temperature became 0° C., stirring was carried out for 3 hours, and the generated crystals were filtered. 8.6 g of a compound 42 was obtained by stirring the crystals in water (10 mL) and methanol (50 mL) for 30 minutes and carrying out filtering.

H-NMR (solvent: CDCl$_3$) δ (ppm):

0.8-1.3 (m, 32H), 1.4-1.6 (m, 4H), 1.7-1.9 (m, 16H), 2.1-2.3 (m, 4H), 2.4-2.6 (m, 2H), 4.2 (t, 2H), 4.3 (t, 2H), 5.8 (dd, 1H), 6.1 (dd, 1H), 6.4 (dd, 1H), 7.0 (d, 1H), 7.2 (dd, 1H), 7.6 (d, 1H)

(Compound 43)

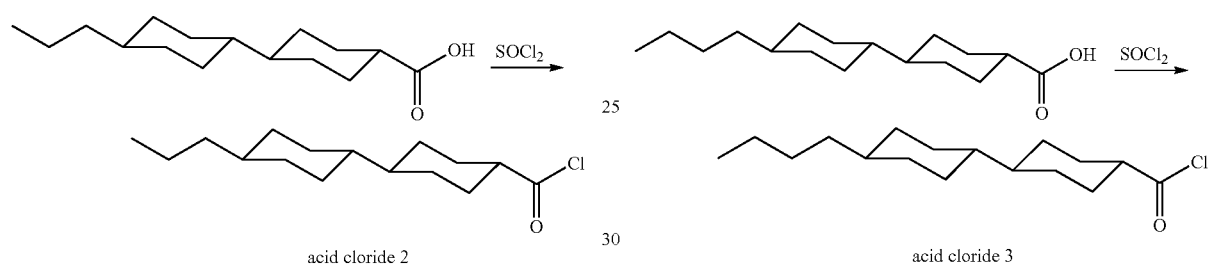

acid cloride 2 — acid cloride 3

4-propylcyclohexyl-4-cyclohexyl carboxylic acid (31 g) was heated to 60° C. after adding toluene (40 mL) and dimethyl formamide (0.3 mL) thereto, thionyl chloride (18 g) was added dropwise thereto, and stirring was carried out for 3 hours at an inner temperature of 60° C. After that, reduced pressure distillation was carried out on the solvent and a carboxylic acid chloride derivative 2 (33 g) was obtained.

4-butylcyclohexyl-4-cyclohexyl carboxylic acid (33 g) was heated to 60° C. after adding toluene (40 mL) and dimethyl formamide (0.3 mL) thereto, thionyl chloride (18 g) was added dropwise thereto, and stirring was carried out for 3 hours at an inner temperature of 60° C. After that, reduced pressure distillation was carried out on the solvent and a carboxylic acid chloride derivative 3 (35 g) was obtained.

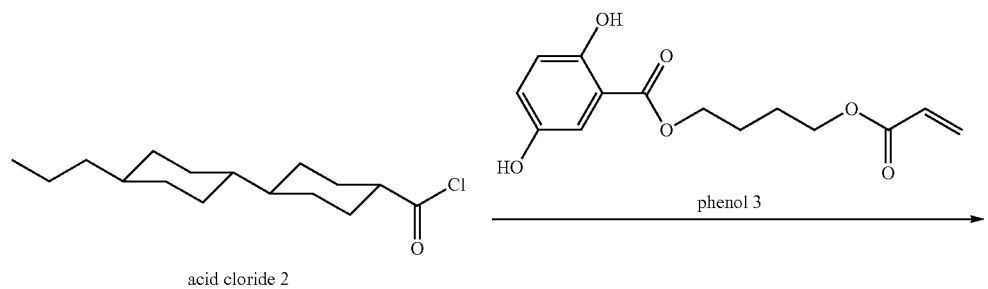

acid cloride 2 phenol 3

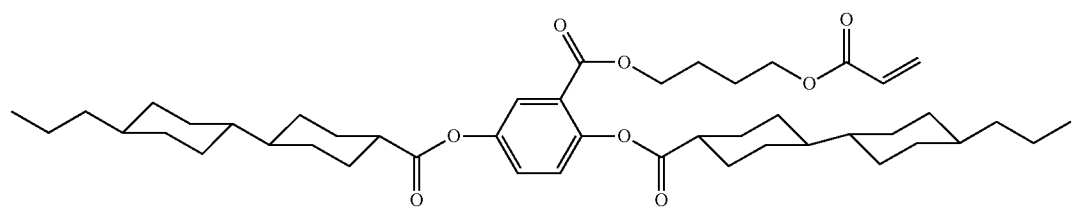

42

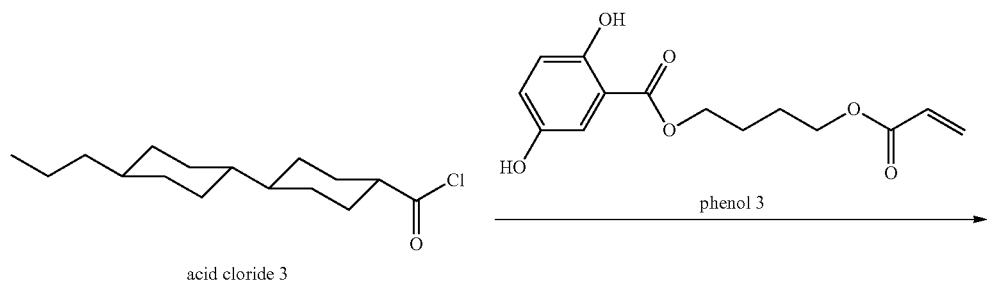

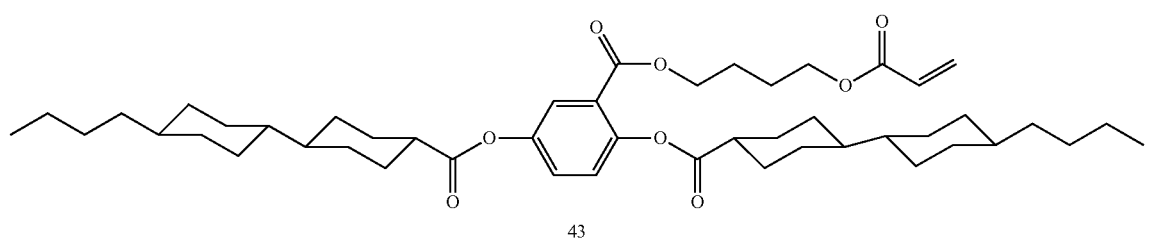

43

The phenol derivative 3 (3.3 g) was stirred in 16 mL of tetrahydrofuran, and dimethylaminopyridine (0.1 g) and the carboxylic acid chloride derivative 3 (6.9 g) were added thereto. The reaction liquid was cooled until the inner temperature became 0° C., triethylamine (3.8 mL) was added dropwise thereto, stirring was carried out for 3 hours at 25° C., and further stirring was carried out for 30 minutes after adding methanol (30 mL) and water (15 mL) thereto. Cooling was carried out until the inner temperature became 0° C., stirring was carried out for 3 hours, and the generated crystals were filtered. 8.9 g of a compound 43 was obtained by stirring the crystals in water (10 mL) and methanol (50 mL) for 30 minutes and carrying out filtering.

H-NMR (solvent: CDCl$_3$) δ (ppm):
0.8-1.3 (m, 36H), 1.4-1.6 (m, 4H), 1.7-1.9 (m, 16H), 2.1-2.3 (m, 4H), 2.4-2.6 (m, 2H), 4.2 (t, 2H), 4.3 (t, 2H), 5.8 (dd, 1H), 6.1 (dd, 1H), 6.4 (dd, 1H), 7.0 (d, 1H), 7.2 (dd, 1H), 7.6 (d, 1H)

(Compound 39)

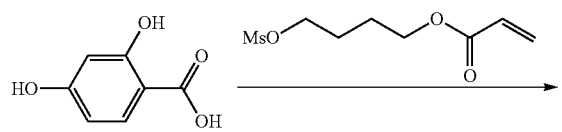

-continued phenol 4

2,4-dihydroxybenzoic acid (10 g) was stirred in dimethylacetamide (50 mL), triethylamine (9.8 mL), 4-acryloyloxy butyl methanesulfonate (11.1 g), and BHT (0.2 g) were added thereto, and stirring was carried out for 10 hours at an inner temperature of 70° C. After cooling the resultant to 30° C., water and ethyl acetate were added thereto, a water layer was removed, and cleansing was carried out using saturated sodium bicarbonate water, dilute hydrochloric acid, and a saline solution in this order. After an organic layer was dried using magnesium sulfate and the drying agent was filtered, reduced pressure distillation was carried out on the solvent after adding BHT (0.1 g), and a phenol derivative 4 was obtained.

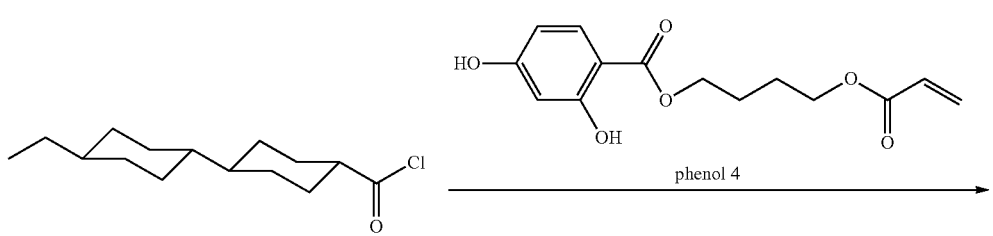

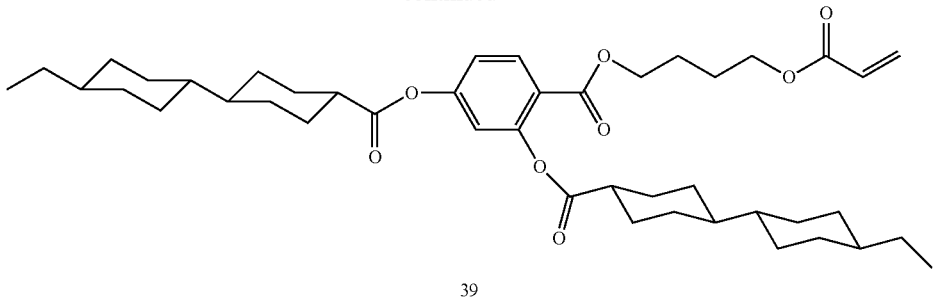

39

The phenol derivative 4 (3.4 g) was stirred in 15 mL of tetrahydrofuran and dimethylaminopyridine (0.1 g) and the carboxylic acid chloride derivative 1 (6.0 g) were added thereto. The reaction liquid was cooled until the inner temperature became 0° C., triethylamine (3.8 mL) was added dropwise thereto, stirring was carried out for 4 hours at 25° C., and further stirring was carried out for 10 minutes after adding water (40 mL). After ethyl acetate was added, a water layer was removed, and cleansing was carried out using saturated sodium bicarbonate water, dilute hydrochloric acid, and a saline solution in this order, the organic layer was dried using magnesium sulfate and the drying agent was filtered. 2.5 g of a compound 39 was obtained by carrying out reduced pressure distillation on the solvent after adding BHT (0.1 g) thereto, performing recrystallization by adding ethyl acetate (10 mL) and methanol (50 mL) thereto, and filtering the generated crystals.

H-NMR (solvent: CDCl$_3$) δ (ppm):

0.8-1.3 (m, 28H), 1.4-1.6 (m, 4H), 1.7-1.9 (m, 16H), 2.1-2.2 (m, 4H), 2.4-2.6 (m, 2H), 4.2 (t, 2H), 4.3 (t, 2H), 5.8 (dd, 1H), 6.1 (dd, 1H), 6.4 (dd, 1H), 6.9 (d, 1H), 7.0 (dd, 1H), 8.0 (d, 1H)

(Compound 25)

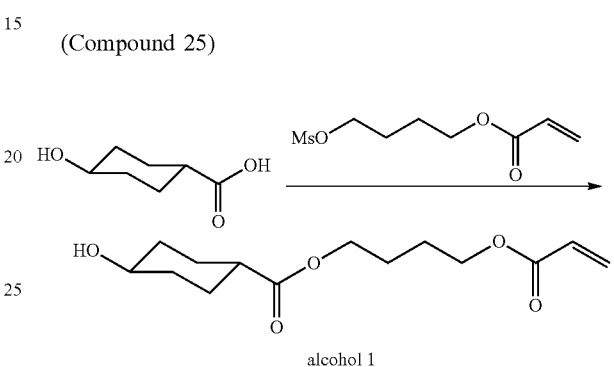

Trans-4-hydroxycyclohexane carboxylic acid (3.2 g) was stirred in dimethylacetamide (10 mL), triethylamine (3.3 mL), 4-acryloyloxy butyl methanesulfonate (4.4 g), and BHT (0.1 g) were added thereto, and stirring was carried out for 6 hours at an inner temperature of 70° C. After cooling the resultant to 30° C., water and ethyl acetate were added thereto, a water layer was removed, and cleansing was carried out using saturated sodium bicarbonate water, dilute hydrochloric acid, and a saline solution in this order. After an organic layer was dried using magnesium sulfate and the drying agent was filtered, reduced pressure distillation was carried out on the solvent after adding BHT (0.1 g) thereto, and an alcohol derivative 1 was obtained.

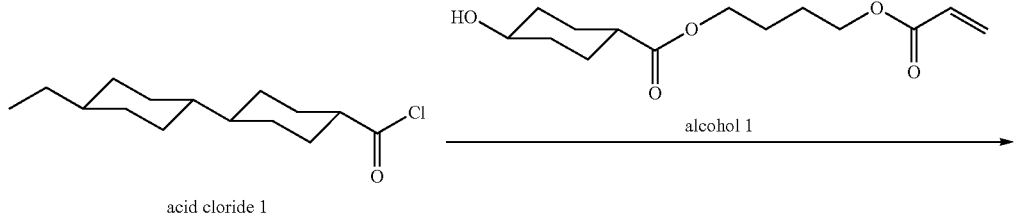

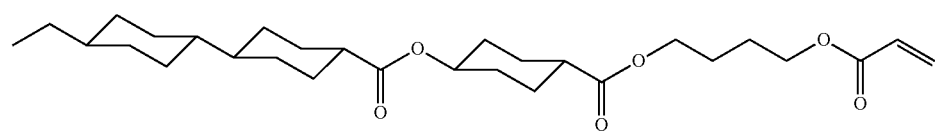

25

The alcohol derivative 1 (3.4 g) was stirred in 18 mL of tetrahydrofuran, and dimethylaminopyridine (0.1 g) and the carboxylic acid chloride derivative 1 (3.7 g) were added thereto. The reaction liquid was cooled until the inner temperature became 0° C., triethylamine (2.3 mL) was added dropwise thereto, stirring was carried out for 5 hours at 25° C., and further stirring was carried out for 30 minutes after adding methanol (30 mL) and water (15 mL) thereto. 2.5 g of a compound 25 was obtained by filtering the crystals which were generated by cooling until the inner temperature became 0° C., performing recrystallization using ethyl acetate (10 mL) and methanol (20 mL), and filtering the generated crystals.

H-NMR (solvent: CDCl$_3$) δ (ppm):

0.7-1.1 (m, 12H), 1.1-1.2 (m, 2H), 1.3-1.4 (m, 4H), 1.5-1.6 (m, 2H), 1.6-1.8 (m, 10H), 1.9-2.1 (m, 6H), 2.1-2.2 (m, 1H), 2.2-2.3 (m, 1H), 4.1 (t, 2H), 4.2 (t, 2H), 4.6-4.7 (m, 1H), 5.8 (dd, 1H), 6.1 (dd, 1H), 6.4 (dd, 1H)

(Compound 40)

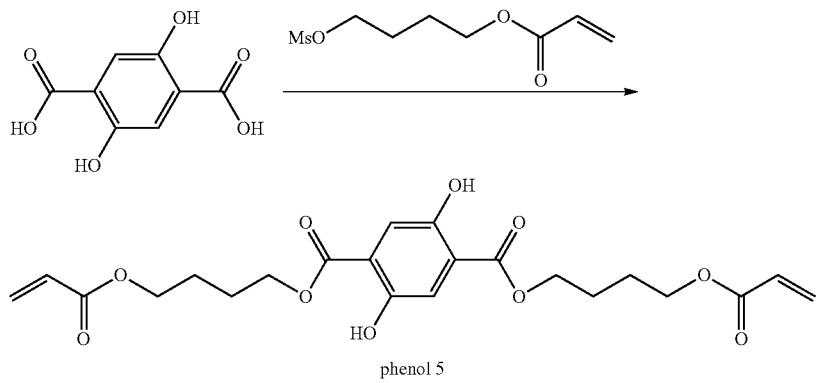

2,5-Dihydroxy terephthalic acid (3.0 g) was stirred in dimethylacetamide (10 mL), triethylamine (4.6 mL), 4-acryloyloxy butyl methanesulfonate (3.7 g), and BHT (0.2 g) were added thereto, and stirring was carried out for 8 hours at an inner temperature of 70° C. After cooling the resultant to 30° C., water and ethyl acetate were added thereto, a water layer was removed, and cleansing was carried out using saturated sodium bicarbonate water, dilute hydrochloric acid, and a saline solution in this order. After an organic layer was dried using magnesium sulfate and the drying agent was filtered, reduced pressure distillation was carried out on the solvent after adding BHT (0.1 g), and a phenol derivative 5 was obtained.

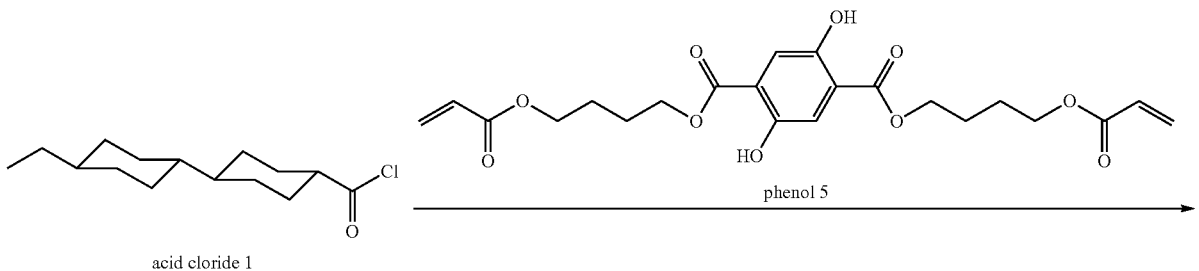

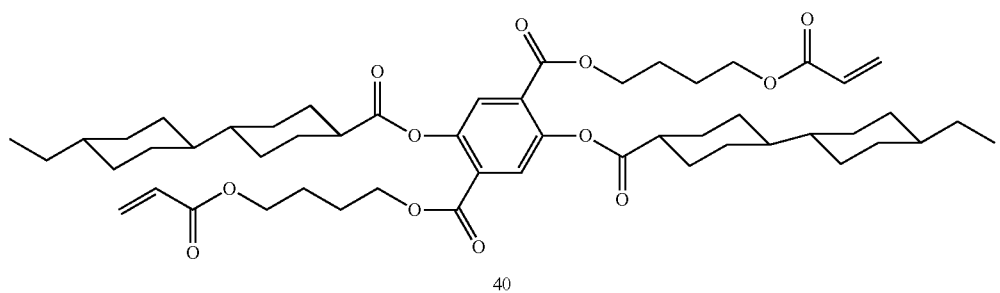

40

The phenol derivative 5 (3.2 g) was stirred in 10 mL of tetrahydrofuran, and dimethylaminopyridine (0.05 g) and the carboxylic acid chloride derivative 1 (3.8 g) were added thereto. The reaction liquid was cooled until the inner temperature became 0° C., triethylamine (2.2 mL) was added dropwise thereto, and stirring was carried out for 3 hours at 25° C. Further stirring was carried out for 30 minutes after adding methanol (20 mL) and the generated crystals were filtered. 4.5 g of a compound 40 was obtained by stirring the crystals in methanol (30 mL) for 30 minutes and carrying out filtering.

H-NMR (solvent: $CDCl_3$) δ (ppm):
0.81.4 (m, 28H), 1.5 (q, 4H), 1.71-0.9 (m, 20H), 2.2-2.3 (m, 4H), 2.5-2.6 (m, 2H), 4.2 (t, 4H), 4.3 (t, 4H), 5.8 (dd, 2H), 6.1 (dd, 2H), 6.4 (dd, 2H), 7.6 (s, 2H)

(Compound 30)

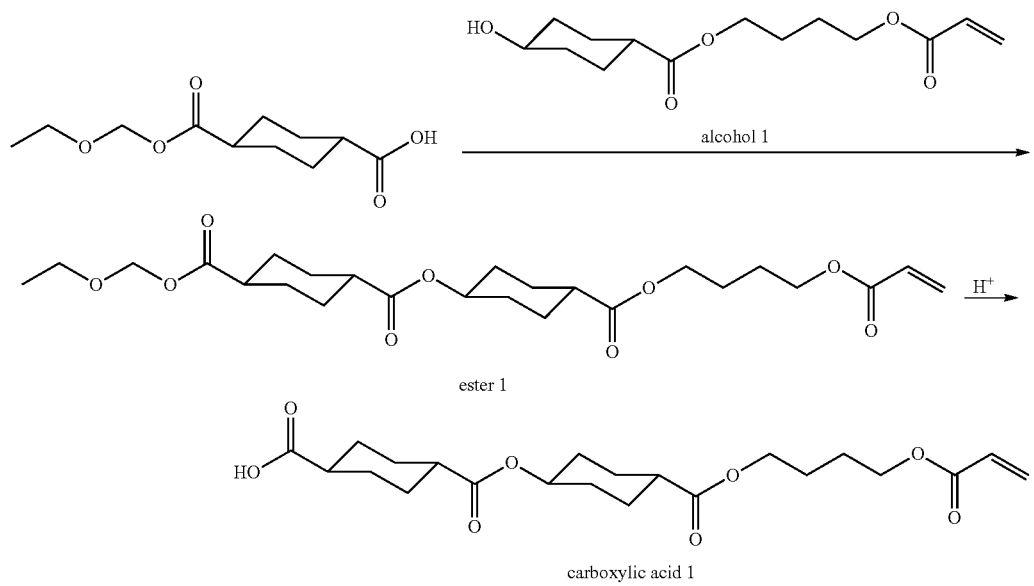

Trans-1,4-cyclohexane dicarboxylic acid monoethoxy methyl ester (1.5 g) was stirred in dimethylacetamide (7 mL), and an alcohol derivative (2.0 g), BHT (0.1 g), and dimethylaminopyridine (0.08 g) were added thereto and cooled to 0° C. Stirring was carried out for 3 hours while gradually adding 1-(3-dimethylamino propyl)-3-ethyl carbodiimide hydrochloride (WSCD HCl) (1.5 g) thereto. After further stirring was carried out for 5 minutes after adding 1M of dilute hydrochloric acid thereto, ethyl acetate was added thereto, a water layer was removed, and cleansing was carried out using dilute hydrochloric acid, saturated sodium bicarbonate water, and a saline solution in this order. After an organic layer was dried using magnesium sulfate and the drying agent was filtered, reduced pressure distillation was carried out on the solvent after adding BHT (0.1 g) thereto.

Next, 7 mL of tetrahydrofuran, 0.12 mL of water, and 0.12 g of p-toluenesulfonic acid monohydrate were added to a reaction composition ester derivative 1 and stirring was carried out for 2 hours at 50° C. A carboxylic acid derivative 1 was obtained by carrying out reduced pressure distillation on the solvent, adding n-hexane, filtering and separating the generated crystals, dissolving the resultant in ethyl acetate, and carrying out purification by silica gel column chromatography.

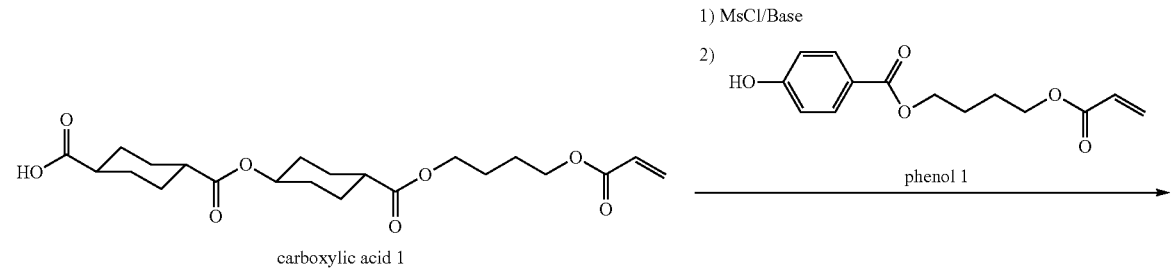

-continued

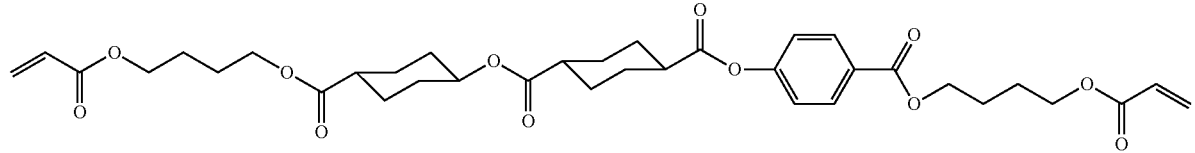

30

A solution where carboxylic acid derivative 1 (1.0 g) was mixed with ethyl acetate (3 mL) and diisopropylethylamine (0.45 mL) was slowly added dropwise to a tetrahydrofuran (4 mL) solution of methanesulfonyl chloride (0.2 mL) on ice. After stirring was carried out for one hour on ice, a tetrahydrofuran (4 mL) solution of dimethylaminolysine (0.03 g) and the phenol derivative 1 (0.72 g) was added dropwise thereto and subsequently, diisopropylethylamine (0.45 mL) was slowly added dropwise thereto on ice. After stirring was carried out for 3 hours at a reaction temperature of 20° C., methanol was added thereto, water and ethyl acetate were further added thereto, a water layer was removed, and cleansing was carried out using saturated sodium bicarbonate water, dilute hydrochloric acid, and a saline solution in this order. After an organic layer was dried using magnesium sulfate and a drying agent was filtered, reduced pressure distillation was carried out on the solvent after adding BHT (0.1 g), and 0.9 g of a compound 30 was obtained by carrying out purification by silica gel column chromatography.

H-NMR (solvent: CDCl$_3$) δ (ppm):
1.3-1.5 (m, 2H), 1.5-1.7 (m, 6H), 1.7-1.8 (m, 4H), 1.8-1.9 (m, 4H), 2.0-2.2 (m, 6H), 2.2-2.4 (m, 4H), 2.5-2.6 (m, 1H), 4.2 (t, 2H), 4.2-4.3 (m, 4H), 4.4 (t, 2H), 4.6-4.8 (m, 1H), 5.8-5.9 (m, 2H), 6.1 (dd, 2H), 6.4 (dd, 2H), 7.1 (d, 2H), 8.0 (d, 2H)

<Measurement of Birefringence>

The birefringence (Δn) of each of the compounds which were synthesized as described above was measured according to the method described on p. 202 in Liquid Crystal Handbook (Liquid Crystal Handbook, Editing Committee). Specifically, Δn at 50° C. was obtained by introducing a liquid crystal composition in which each of the compounds which were synthesized as described above were mixed according to Table 1 into a wedge type cell, and measuring intervals of a stripe pattern which was observed under crossed nicols conditions under light with a wavelength of 550 nm. The results are shown in Table 1.

TABLE 1

| | | | Type of additive agent | | | |
|---|---|---|---|---|---|---|
| Liquid crystal composition | Compound | Added amount (parts by mass) | Compound 1 (parts by mass) | Compound 2 (parts by mass) | M-1 (parts by mass) | Δn (50° C.) |
| 1 | 1 | 66 | | | 33 | 0.114 |
| 2 | 1 | 33 | | | 66 | 0.144 |
| 3 | 2 | 33 | | | 66 | 0.127 |
| 4 | 1 | 60 | | 40 | | 0.077 |
| 5 | 1 | 40 | | 60 | | 0.066 |
| 6 | 25 | 50 | 60 | 40 | | 0.066 |
| 7 | 32 | 50 | 60 | 40 | | 0.078 |
| 8 | 32 | 50 | | 50 | | 0.065 |
| 9 | 39 | 25 | 60 | 40 | | 0.071 |
| 10 | 40 | 50 | 60 | 40 | | 0.065 |
| 11 | 42 | 50 | 60 | 40 | | 0.079 |
| 12 | 43 | 50 | 60 | 40 | | 0.078 |
| 13 | 30 | 50 | 60 | 40 | | 0.070 |
| 101 (Comparative Example) | M-1 | 100 | | | | 0.175 |
| 102 (Comparative Example) | M-2 | 33 | | | 66 | 0.150 |

M-1
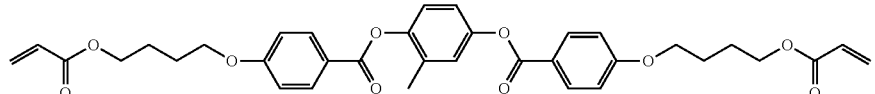

M-2
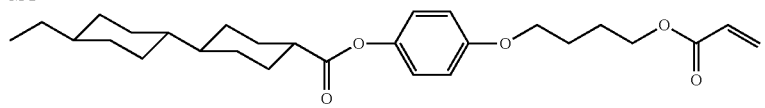

<Confirmation of Solubility>

As a result of measuring out 0.2 g of the compound 1 and gradually adding methylethyl ketone (MEK) and measuring the concentration at which complete dissolution occurred at room temperature, the MEK solubility of the compound 1 was 25%. On the other hand, as a result of performing the same experiment with respect to the compound M-2 in Comparative Example, the MEK solubility was 1%.

<Forming Retardation Film>

A polymerizable composition coating liquid (1) with the composition below was prepared using the exemplified compounds which were synthesized as described above.

| (Polymerizable composition coating liquid (1)) | |
|---|---|
| Compound (1) | 60 parts by mass |
| Compound (2) | 40 parts by mass |
| Air interface alignment agent (1) | 0.1 parts by mass |
| Polymerization Initiator IRGACURE 819 (manufactured by BASF Corporation) | 3 parts by mass |
| Solvent chloroform | 120 parts by mass |

Air Interface Alignment Agent (1)

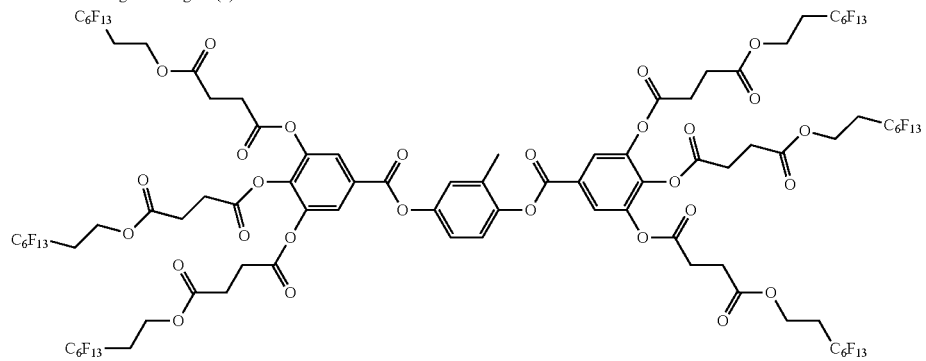

Next, a cleansed glass substrate was coated with a polyimide alignment film SE-130 manufactured by Nissan Chemical Industries, Ltd. by a spin coating method and firing was carried out at 250° C. for one hour after drying. A rubbing treatment was carried out thereon and a substrate with an alignment film attached thereto was produced. After a rubbing treated surface of the alignment film was coated with the polymerizable composition coating liquid (1) at room temperature by a spin coating method and alignment and aging were carried out at 80° C. for 30 seconds, a retardation film 1 was formed by irradiation with light under a nitrogen gas atmosphere at 50° C. for 10 seconds using a high pressure mercury lamp and fixing the alignment. After coating and before heating, the precipitation of crystals was not seen on the coated film.

When the retardation film 1 which was obtained by aligning and fixing the polymerizable composition was observed using a polarizing microscope, it was possible to confirm that there were no alignment defects and that the phase film 1 was evenly aligned uniaxially. As a result of further measuring the film using AxoScan manufactured by Axometrics, Inc, in the Tip-Tilt mode, it was confirmed that the average inclined angle of the liquid crystal which was calculated by the apparatus was 0.8 degrees and an A-plate type retardation film could be formed. In addition, Δn at a wavelength of 550 nm which was calculated from the phase difference which was measured using the apparatus and the film thickness of the retardation film which was measured using a confocal laser film thickness measuring apparatus (FV-7510 manufactured by Keyence Corporation) was 0.061.

In the polymerizable composition coating liquid (1), retardation films 2 to 5 and 101 were produced in the same manner as the production of the retardation film 1 using a polymerizable composition coating liquid in which the compound (1) and the compound (2) were changed to the mass ratios or the compounds in Table 2, and Δn was measured in the same manner as the measurement of the retardation film 1. The results are shown in Table 2.

Regarding the retardation films 1 to 5, the precipitation of crystals was not seen on the coated film after being coated and before being polymerized; however, regarding the retardation film 101, the precipitation of crystals was generated after being coated and before being polymerized and roughness was generated on the surface of the retardation film.

TABLE 2

| | | Added amount (parts by mass) | Type of additive agent | | |
|---|---|---|---|---|---|
| Retardation film | Compound | | Compound 1 (parts by mass) | Compound 2 (parts by mass) | Δn |
| 1 | — | — | 60 | 40 | 0.061 |
| 2 | — | — | 40 | 60 | 0.053 |
| 3 | 32 | 33 | 40 | 27 | 0.059 |
| 4 | 32 | 30 | 20 | 50 | 0.058 |
| 5 | 32 | 50 | | 50 | 0.053 |
| 101 (Comparative Example) | M1 | 100 | | | 0.161 |

<Forming Cholesteric Film>

A polymerizable composition coating liquid (2) with the composition below was prepared using the exemplified compounds which were synthesized as described above.

| (Polymerizable composition coating liquid (2)) | |
|---|---|
| Compound (1) | 60 parts by mass |
| Compound (2) | 40 parts by mass |
| Chiral Agent LC-756 (manufactured by BASF Corporation) | 6.6 parts by mass |
| Air interface alignment agent (1) | 0.1 parts by mass |
| Polymerization Initiator IRGACURE 819 (manufactured by BASF Corporation) | 3 parts by mass |
| Solvent chloroform | 100 parts by mass |

After a rubbing treated surface of a substrate with a polyimide alignment film which was produced in the same manner as the one which was used when forming the retardation film was coated with the polymerizable composition coating liquid (2) by a spin coating method at room temperature and alignment and aging were carried out at 70° C. for 1 minute after being at 90° C. for 20 seconds, a selective reflection film 1 was formed by fixing the alignment by irradiating light at 60° C. under a nitrogen gas atmosphere for 10 seconds using a high pressure mercury lamp. After being coated and before being polymerized, the precipitation of crystals was not seen on the coated film. In addition, the thickness of the coated film was 5.2 μm.

When the selective reflection film 1 was observed using a polarizing microscope, it was possible to confirm that there were no alignment defects and that the selective reflection film 1 was evenly aligned. When the transmission spectrum of the film was further measured using a spectrophotometer UV-3100 PC manufactured by Shimadzu Corporation, there was a selective reflection peak which had a center at 570 nm and the half-value width thereof was 39 nm. The ratio (Δλ/λ) of the half-value width of the selective reflection wavelength region and the center wavelength of the selective reflection was 0.068.

The obtained transmission spectrum is shown in FIG. 1.

In addition, a comparative example polymerizable composition coating liquid (3) with the composition below was prepared using the exemplified compounds which were synthesized as described above.

| (Polymerizable composition coating liquid (3)) | |
| --- | --- |
| Compound (M1) | 100 parts by mass |
| Chiral agent LC-756 | 5.4 parts by mass |
| (manufactured by BASF Corporation) | |
| Air interface alignment agent (1) | 0.1 parts by mass |
| Polymerization Initiator IRGACURE 819 | 3 parts by mass |
| (manufactured by BASF Corporation) | |
| Solvent chloroform | 150 parts by mass |

A selective reflection film 101 (Comparative Example) was formed in the same manner as the forming of the selective reflection film 1 apart from using the polymerizable composition coating liquid (3) instead of the polymerizable composition coating liquid (2). Regarding the selective reflection film 101, the precipitation of crystals was generated after being coated and before being polymerized and roughness was generated on the surface of the reflection film.

When the transmission spectrum of the selective reflection film 101 was measured, there was a selective reflection peak which had a center at 569 nm and the half-value width thereof was 71 nm. The ratio (Δλ/λ) of the half-value width of the selective reflection wavelength region and the center wavelength of the selective reflection was 0.125.

<Production of Visible Light Reflection Film>

A polymerizable composition coating liquid (4) with the composition below was prepared using the exemplified compounds which were synthesized as described above.

| (Polymerizable composition coating liquid (4)) | |
| --- | --- |
| Compound (32) | 50 parts by mass |
| Compound (2) | 50 parts by mass |
| Trimethylolpropane triacrylate | 5 parts by mass |
| Chiral agent LC-756 | 5.8 parts by mass |
| (manufactured by BASF Corporation) | |
| Air interface alignment agent (1) | 0.03 parts by mass |

| (Polymerizable composition coating liquid (4)) | |
| --- | --- |
| Polymerization Initiator IRGACURE 819 | 3 parts by mass |
| (manufactured by BASF Corporation) | |
| Solvent cyclohexanone | 260 parts by mass |

A rubbing treated surface of PET manufactured by Fujifilm Corporation on which a rubbing treatment was carried out was coated with the polymerizable composition coating liquid (4) at room temperature using a wire bar such that the thickness of the dry film after being dried was 5.2 μm. After drying the coated layer at room temperature for 10 seconds, heating was carried out in an atmosphere of 100° C. for 2 minutes, aging was carried out at 70° C. for 2 minutes after that, UV irradiation was carried out at the same temperature using a D BULB (lamp 90 mW/cm) manufactured by Heraeus K. K. Noblelight Division at an output of 80% for 8 seconds and the selective reflection film 1 was obtained. After coating and before heating, the precipitation of crystals was not seen on the coated film.

When the selective reflection film 1 was observed using a polarizing microscope, it was possible to confirm that there were no alignment defects and that the selective reflection film 1 was evenly aligned. When the transmission spectrum of the film was further measured using a spectrophotometer UV-3100 PC manufactured by Shimadzu Corporation, there was a selective reflection peak which had a center at 550 nm and the half-value width thereof was 29 nm. The ratio (Δλ/λ) of the half-value width of the selective reflection wavelength region and the center wavelength of the selective reflection was 0.053.

Figure 2:
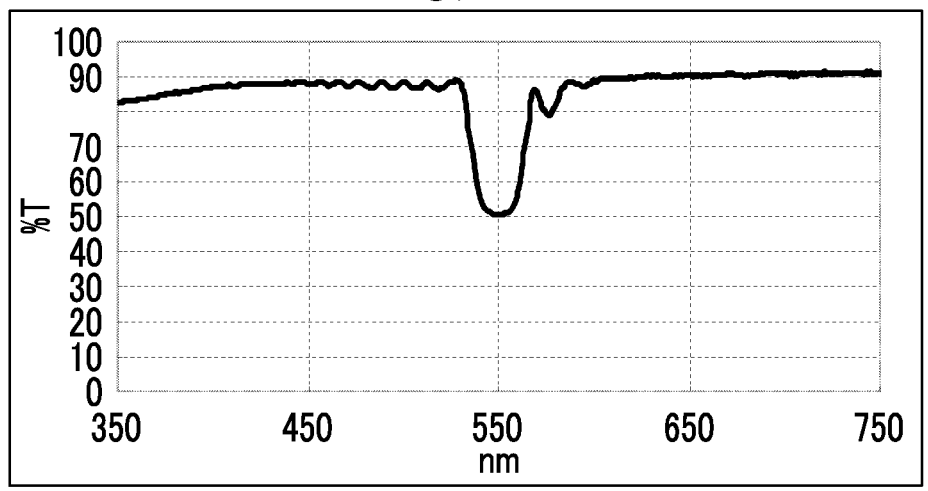
FIG. 2 is a diagram which shows the transmission spectrum of a selective reflection film 1 which is produced in Examples.

The obtained transmission spectrum is shown in FIG. 2.

Polymerizable composition coating liquids (5) and (6) with the compositions below were prepared in the same manner as the polymerizable composition coating liquid (4).

| (Polymerizable composition coating liquid (5)) | |
| --- | --- |
| Compound (32) | 50 parts by mass |
| Compound (2) | 50 parts by mass |
| Trimethylolpropane triacrylate | 5 parts by mass |
| Chiral agent LC-756 | 5.0 parts by mass |
| (manufactured by BASF Corporation) | |
| Air interface alignment agent (1) | 0.03 parts by mass |
| Polymerization Initiator IRGACURE 819 | 3 parts by mass |
| (manufactured by BASF Corporation) | |
| Solvent cyclohexanone | 260 parts by mass |

| (Polymerizable composition coating liquid (6)) | |
| --- | --- |
| Compound (32) | 50 parts by mass |
| Compound (2) | 50 parts by mass |
| Trimethylolpropane triacrylate | 5 parts by mass |
| Chiral agent LC-756 | 7.2 parts by mass |
| (manufactured by BASF Corporation) | |
| Air interface alignment agent (1) | 0.03 parts by mass |
| Polymerization Initiator IRGACURE 819 | 3 parts by mass |
| (manufactured by BASF Corporation) | |

Solvent Cyclohexanone 260 Parts by Mass

A rubbing treated surface of PET manufactured by Fujifilm Corporation on which a rubbing treatment was carried out was coated with the polymerizable composition coating liquid (5) at room temperature using a wire bar such that the thickness of the dry film after being dried was 6.0 μm. After drying the coated layer at room temperature for 10 seconds, heating was carried out in an atmosphere of 100° C. for 2 minutes, aging was carried out at 70° C. for 2 minutes after that, UV irradiation was carried out at the same temperature using a D BULB (lamp 90 mW/cm) manufactured by Heraeus K. K. Noblelight Division at an output of 80% for 8 seconds and the selective reflection film 2 was obtained. After coating and before heating, the precipitation of crystals was not seen on the coated film When the selective reflection film 2 was observed using a polarizing microscope, it was possible to confirm that there were no alignment defects and that the selective reflection film 2 was evenly aligned. When the transmission spectrum of the film was further measured using a spectrophotometer UV-3100 PC manufactured by Shimadzu Corporation, there was a selective reflection peak which had a center at 651 nm and the half-value width thereof was 33 nm. The ratio ($\Delta\lambda/\lambda$) of the half-value width of the selective reflection wavelength region and the center wavelength of the selective reflection was 0.051.

A rubbing treated surface of PET manufactured by Fujifilm Corporation on which a rubbing treatment was carried out was coated with the polymerizable composition coating liquid (6) at room temperature using a wire bar such that the thickness of the dry film after being dried was 4.8 µm. After drying the coated layer at room temperature for 10 seconds, heating was carried out at an atmosphere of 100° C. for 2 minutes, aging was carried out at 70° C. for 2 minutes after that, UV irradiation was carried out at the same temperature using a D BULB (lamp 90 mW/cm) manufactured by Heraeus K. K. Noblelight Division at an output of 80% for 8 seconds and the selective reflection film 3 was obtained. After coating and before heating, the precipitation of crystals was not seen on the coated film.

When the selective reflection film 3 was observed using a polarizing microscope, it was possible to confirm that there were no alignment defects and the selective reflection film 3 was evenly aligned. When the transmission spectrum of the film was further measured using a spectrophotometer UV-3100 PC manufactured by Shimadzu Corporation, there was a selective reflection peak which had a center at 453 nm and the half-value width thereof was 25 nm. The ratio ($\Delta\lambda/\lambda$) of the half-value width of the selective reflection wavelength region and the center wavelength of the selective reflection was 0.055.

Production of Laminate of Visible Light Reflection Layer

The selective reflection layer side of the selective reflection film 1 was coated with a UV curing type adhesive Exp. U12034-6 manufactured by DIC Corporation at room temperature using a wire bar such that the thickness of the dry film after being dried was 5 µm. The coated surface and the surface on the selective reflection layer side of the selective reflection film 2 which was produced as described above were adhered together such that air bubbles did not enter therebetween, UV irradiation was carried out at 30° C. using a D BULB (lamp 90 mW/cm) manufactured by Heraeus K. K. Noblelight Division at an output of 60% for 6 seconds to 12 seconds after that, and the PET film on the selective reflection film 1 side was peeled off. Subsequently, the peeled off surface was coated with a UV curing type adhesive Exp. U12034-6 manufactured by DIC Corporation at room temperature using a wire bar such that the thickness of the dry film after being dried was 5 µm. The coated surface and the surface on the selective reflection layer side of the selective reflection film 3 which was produced as described above were adhered such that air bubbles did not enter, UV irradiation was carried out at 30° C. using a D BULB (lamp 90 mW/cm) manufactured by Heraeus K. K. Noblelight Division at output 60% for 6 seconds to 12 seconds, after that, the PET film on the selective reflection film 3 side was peeled off, and the laminated film 4 of the visible light reflection layer was produced.

Figure 3:
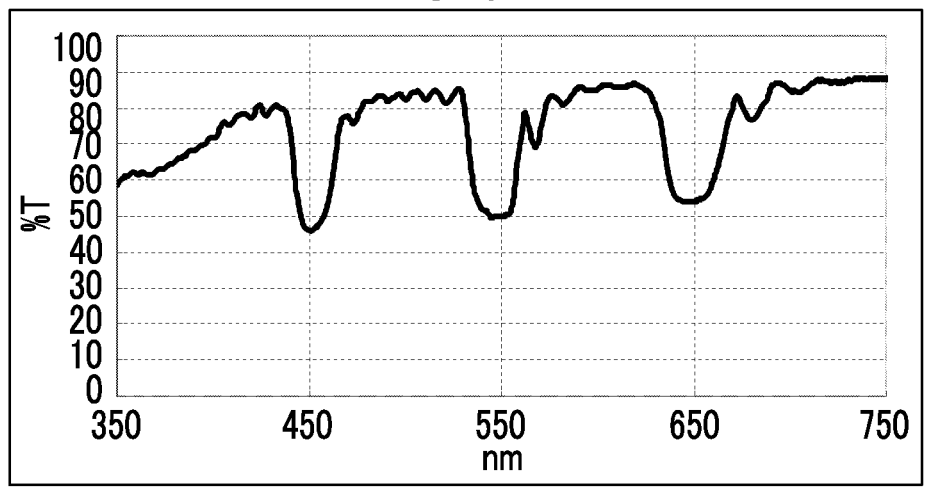
FIG. 3 is a diagram which shows the transmission spectrum of a laminated film 4 which is produced in Examples.

When the transmission spectrum of the film was measured using spectrophotometer UV-3100 PC manufactured by Shimadzu Corporation, it was understood that there were reflection peaks at 450 nm, 550 nm, and 650 nm and that the film had a high visible light transmittance of 70% or more. The obtained transmission spectrum is shown in FIG. 3.

<Production of Half Mirror 1>

The selective reflection layer side of the laminated film 4 of the visible light reflection layer was coated with a UV curing type adhesive Exp. U12034-6 manufactured by DIC Corporation at room temperature using a wire bar such that the thickness of the dry film after being dried was 5 µm. In a state of being installed between orthogonal polarizing plates, a half mirror 1 for displaying a projection image with visible light transmittance was produced on an acryl substrate by adhering a transparent substrate ("ACRYLITE L" manufactured by Mitsubishi Rayon Co., Ltd.) surface made of methacryl with a thickness of 5 mm and a maximum phase difference of 5 nm in-plane of 10 cm square where it was not possible to view color variation in-plane and an adhesive coating surface of the laminated film 4 of the visible light reflection layer, applying UV irradiation, and peeling off the PET film of the film 4.

<Production of Half Mirror 2 with Anti-Reflection Layer>

A film with an anti-reflection layer with a surface reflection rate of 0.4% in 550 nm where a hard coat layer with a refractive index of 1.52 and a thickness of 3.0 µm was formed on a TAC film with a thickness of 40 µm, a layer of intermediate refractive index with a refractive index of 1.594 and a thickness of 0.06 µm was formed on the hard coat layer, a layer of high refractive index with a refractive index of 1.708 and a thickness of 0.13 µm was formed on the layer of intermediate refractive index, and a layer of low refractive index with a refractive index of 1.343 and a thickness of 0.094 µm was formed on the layer of high refractive index, as anti-reflection layers, was prepared. The TAC film side was coated with a UV curing type adhesive Exp. U12034-6 manufactured by DIC Corporation at room temperature using a wire bar such that the thickness of the dry film after being dried was 5 µm. The coated surface and the surface on the liquid crystal layer side of the laminated film 4 of the visible light reflection layer which was produced as described above were adhered together such that air bubbles did not enter, UV irradiation was carried out at 30° C. using a D BULB (lamp 90 mW/cm) manufactured by Heraeus K. K. Noblelight Division at an output of 60% for 6 seconds to 12 seconds after that, and a visible light reflection film 5 with an anti-reflection layer was produced by peeling off the PET film of the film 4 after that.

Next, the surface of the liquid crystal layer side of the visible light reflection film 5 was coated with a UV curing type adhesive Exp. U12034-6 manufactured by DIC Corporation at room temperature using a wire bar such that the thickness of the dry film after being dried was 5 µm. A half mirror 2 for displaying a projection image which has an acryl substrate, a visible light reflection layer, and an anti-reflection layer in this order was produced by, in a state of being installed between orthogonal polarizing plates, adhering a transparent substrate ("ACRYLITE L" manufactured by Mitsubishi Rayon Co., Ltd.) surface made of methacryl with a thickness of 5 mm and a maximum phase difference of 5 nm in-plane of 10 cm square where it was not possible to view color variation in-plane and an adhesive coating surface of the visible light reflection film and applying UV irradiation.

What is claimed is:

1. A polymerizable compound which is represented by Formula (I):

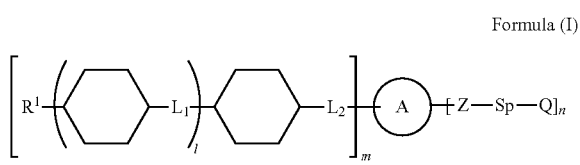

Formula (I)

wherein, in the formula,
$R^1$ indicates a straight-chain or branched alkyl group with 1 to 12 carbon atoms,

the moiety indicated above is a group which is obtained by removing (m+n) hydrogen atoms from benzene,
$L_1$ indicates a single bond, —COO—, or —OCO—,
$L^2$ indicates —COO— or —CONR$^2$—,
Z indicates a single bond, —O—, —NH—, —N(CH$_3$)—, —S—, —COO—, —OCO—, —OCOO—, or —CONR$^2$—,
$R^2$ indicates a hydrogen atom or -Sp-Q,
Sp indicates a straight-chain or branched alkylene group with 1 to 12 carbon atoms which may be substituted with Q, or a linking group which is obtained by substituting any one or more of —CH$_2$— with —O—, —S—, —NH—, —N(Q)-, or —CO— in a straight-chain or branched alkylene group with 1 to 12 carbon atoms which may be substituted with Q,
Q indicates a hydrogen atom or a (meth)acryloyl group,
l indicates an integer of 1,
m indicates an integer of 1 or 2,
n indicates an integer of 1 to 3,
a plurality of $R^1$'s, a plurality of $L_1$'s, a plurality of $L_2$'s, a plurality of Z's, a plurality of Sp's, and a plurality of Q's may be each the same as or different from each other, and
as —Z-Sp-Q, at least one group where Z is —COO— or —CONR$^2$— and Q is a (meth)acryloyl group is included.

2. The polymerizable compound according to claim 1, wherein all of $L_1$'s are single bonds.

3. The polymerizable compound according to claim 1, wherein all of Q's are (meth)acryloyl groups.

4. The polymerizable compound according to claim 1, wherein all of $R^1$'s are straight-chain alkyl groups.

5. The polymerizable compound according to claim 1, wherein all of $R^1$'s are straight-chain alkyl groups, all of $L_1$'s are single bonds, all of $L_2$'s are —COO—, and all of Q's are (meth)acryloyl groups.

6. The polymerizable compound according to claim 5, wherein m is 1, n is 1 or 2, and at least one of Z is —COO—.

7. The polymerizable compound according to claim 5, wherein m is 2, n is 1, and Z is —COO— or —CONR$^2$—.

8. A polymerizable composition comprising:
the polymerizable compound according to claim 1.

9. The polymerizable composition according to claim 8, further comprising:
another polymerizable liquid crystal compound other than the polymerizable compound which is represented by Formula (I).

10. The polymerizable composition according to claim 8, further comprising:
a cross-linking agent.

11. The polymerizable composition according to claim 8, further comprising:
two or more types of polymerizable compounds which are represented by Formula (I).

12. The polymerizable composition according to claim 8, further comprising:
a chiral compound.

13. A film comprising:
a layer which is formed from the polymerizable composition according to claim 8.

14. A film comprising:
two or more layers which are formed from the polymerizable composition according to claim 8.

15. The film according to claim 13, wherein selective reflection is exhibited, and $\Delta\lambda/\lambda$ which is a ratio of a half-value width $\Delta\lambda$ of a wavelength region of the selective reflection to a center wavelength $\lambda$ of the selective reflection is 0.09 or less.

16. A film comprising:
at least three layers which are formed from the polymerizable composition according to claim 8, wherein the three layers are a layer in which a cholesteric liquid crystalline phase which has a center wavelength of selective reflection in a red light wavelength region is fixed, a layer in which a cholesteric liquid crystalline phase which has a center wavelength of selective reflection in a green light wavelength region is fixed, and a layer in which a cholesteric liquid crystalline phase which has a center wavelength of selective reflection in a blue light wavelength region is fixed.

17. A half mirror for displaying a projection image comprising:
the film according to claim 16.

18. The half mirror for displaying a projection image according to claim 17, further comprising:
a substrate which is inorganic glass or an acrylic resin.

19. The half mirror for displaying a projection image according to claim 17, further comprising:
an anti-reflection layer on an uppermost surface.

20. The polymerizable compound according to claim 1, wherein all of $R^1$'s are an ethyl group or an n-butyl group.

* * * * *